United States Patent
Frisch et al.

(10) Patent No.: US 6,653,068 B2
(45) Date of Patent: Nov. 25, 2003

(54) GENERATION OF SPECIFIC BINDING PARTNERS BINDING TO (POLY)PEPTIDES ENCODED BY GENOMIC DNA FRAGMENTS OR ESTS

(75) Inventors: Christian Frisch, Planegg (DE); Titus Kretzschmar, München (DE); Adolf Höss, Weyarn (DE); Thomas Von Rüden, Planegg (DE)

(73) Assignee: Morphosys AG (DE)

( * ) Notice: Subject to any disclaimer, the term of this patent is extended or adjusted under 35 U.S.C. 154(b) by 0 days.

(21) Appl. No.: 09/795,872

(22) Filed: Feb. 28, 2001

(65) Prior Publication Data

US 2003/0170622 A1 Sep. 11, 2003

Related U.S. Application Data

(63) Continuation of application No. PCT/EP00/06137, filed on Jun. 30, 2000.

(51) Int. Cl.$^7$ ............................. C12Q 1/70; C12Q 1/68; G01N 33/53; C12P 21/04; C12N 15/00; C12N 15/09; C12N 15/63; C12N 15/70; A23J 1/00; C07K 1/00; C07K 14/00; C07K 16/00; C07K 17/00

(52) U.S. Cl. ................................. 435/5; 435/6; 435/7.1; 435/69.7; 435/71.1; 435/71.2; 435/320.1; 530/412

(58) Field of Search ............................. 435/5; 431/5, 6, 431/7.1, 69.7, 71.1, 71.2, 320.1; 530/412

(56) References Cited

U.S. PATENT DOCUMENTS

| | | | | | |
|---|---|---|---|---|---|
| 5,814,477 A | * | 9/1998 | Williams et al. | ........ | 435/252.33 |
| 5,895,651 A | * | 4/1999 | Simmons et al. | ........ | 424/185.1 |
| 5,989,554 A | * | 11/1999 | Knuth et al. | ............. | 424/192.1 |

FOREIGN PATENT DOCUMENTS

WO    WO 98/30684    7/1998

OTHER PUBLICATIONS

Guan, C. et al., "Vectors that facilitate the expression and purification of foreign peptides in *Escherichia coli* by fusion to maltose–binding protein", Gene, vol. 67, pp. 21–30 (1988).*

Maina, C. V. et al., "An *Escherichia coli* vector to express and purify foreign proteins by fusion to and separation from maltose–binding protein", Gene, vol. 74, pp. 365–373 (1988).*

Rudolph, R. et al., "In vitro folding of inclusion body proteins", FASEB J., vol. 10, pp. 49–56 (1996).*

Marczinovits, I. et al., "An alternative purification protocol for producing hepatatis B virus X antigen on a preparative scale in *Escherichia coli*", J. Biotechnology, vol. 56, pp. 81–88 (1997).*

Nandi, A. et al., "Expression of the Extracellular Domain of the Human Heat–Stable Enterotoxin Receptor in *Escherichia coli* and Generation of Neutralizing Antibodies", Protein Expression and Purification, vol. 8, pp. 151–159 (1996).*

Vaughan, T.J., et al., "Human Antibodies with Sub–nanomolar Affinities Isolated from a Large Non–immunized Phage Display Library", Nature Biotech., vol. 14, pp. 309–314 (1996).*

C. Krebber et al., "Selectively–infective phage (SIP): A mechanistic dissection of a novel in vivo selection for protein–ligand interactions", J. Mol. Biol. (1997) 268, 607–618.

L. Persic et al., "Single–chain variable fragments selected on the 57–76 p21 Ras neutralising epitope from phage antibody libraries recognise the parental protein", FEBS Letters (1999) 443, 112–116. Only pp. 112, 114, 116.

Y. Hitomi et al., "High efficiency prokaryotic expression and purification of a portion of the Hepatitis C core protein and analysis of the immune response to recombinant protein in BALB/c mice", Viral Immunology (1995) 8, 109–119.

G. Hagendorff et al., "A monoclonal antibody generated against a recombinant peptide fragment of the B3 domain of carcinoembryonic antigen reacts with intact carcinoembryonic antigen reacts with intact carcinoembryonic antigen", Biochemica et Biophysica Acta (1995) 1260, 259–268.

H. Takemura et al., "Cloning and expression of human defensin HNP–1 genomic DNA in *Escherichia coli*", Journal of Microbiological Methods (1996) 25, 287–293.

R. Rudolph and H. Lillie, "In Vitro folding of inclusion body proteins", The FASEB Journal (1996) 10, 49–56.

(List continued on next page.)

Primary Examiner—Kenneth R. Horlick
Assistant Examiner—Teresa Strzelecka
(74) Attorney, Agent, or Firm—Heller Ehrman White and McAuliffe

(57) ABSTRACT

The present invention relates to the generation of specific binding partners binding to (poly)peptides encoded by genomic DNA fragments or ESTs. The (poly)peptides are expressed as part of fusion proteins which are forming inclusion bodies on expression in host cells. The inclusion bodies are used to generate binding partners which bind specifically to said (poly)peptides. The specific binding partners, in particular immunoglobulins or fragments thereof, are useful for analysis and functional characterization of proteins encoded by nucleic acid sequences comprising the corresponding genomic DNA fragments or ESTs. The invention further relates to nucleic acid molecules, vectors and host cells to be used in the methods of the present invention. The invention further relates to the use of fusion proteins comprising the first N-terminal domain of the geneIII protein of filamentous phage as fusion partner for the expression of a (poly)peptide/protein fused to said fusion partner, and to methods for the expression of (poly)peptide/proteins.

32 Claims, 10 Drawing Sheets

OTHER PUBLICATIONS

Figure 1A:
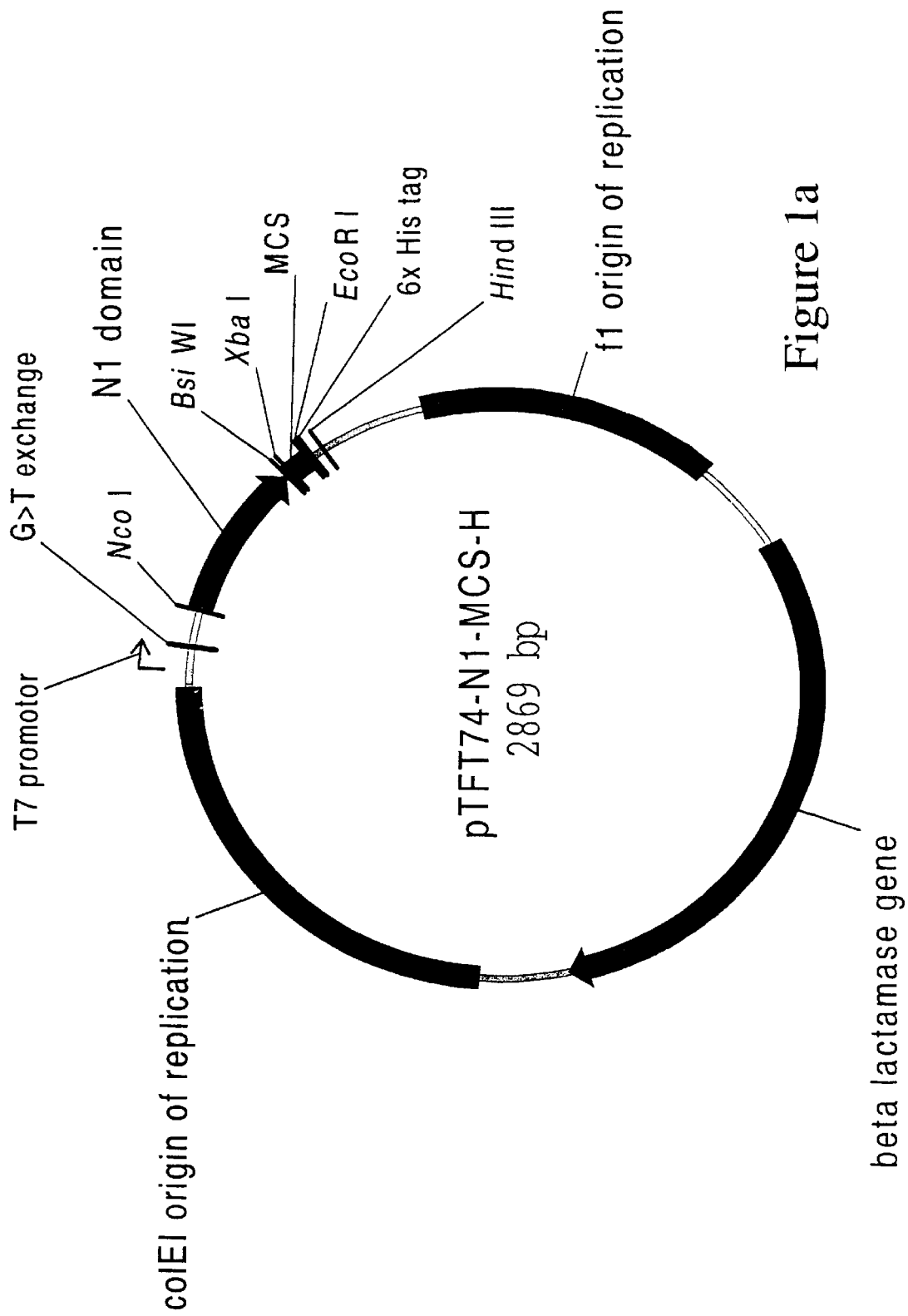

S. Makrides, "Strategies for Achieving High–Level Expression of Genes in *Escherichia coli*", Microbiological Review (1996) 512–538.

C. Schein, "Solubility as a function of protein structure and solvent components", Bio/Technology vol. 8, (1990) 308–317.

D. Wilkinson et al., "Predicting the solubility of recombinant proteins in *Escherichia coli*", Bio/Technology vol. 9 (1991) 443–448.

Jean–Michel Betton et al., "Folding of a Mutant Maltose–binding Protein of *Escherichia coli* Which Forms Inclusion Bodies", The Journal of Biological Chemistry, Apr. 5, 1996, pp. 8046–8052, vol. 271, No. 14, The American Society for Biochemistry and Molecular Biology, Inc.

Deb K. Chatterjee et al., "Cloning and overexpression of the gene encoding bacteriophage T5 DNA polymerase", Gene, 1991, pp. 13–19, vol. 97, Elsevier Science Publishers.

Glen A. Coburn et al., "Overexpression, Purification, and Properties of *Escherichia coli* Ribonuclease II", The Journal of Biological Chemistry, Jan. 12, 1996, pp. 1048–1053, vol. 271, No. 2, The American Society for Biochemistry and Molecular Biology, Inc.

Niek Dekker et al., "In vitro folding of *Escherichia coli* outer–membrane phospholipase A", Eur. J. Biochem., 1995, pp. 214–219, vol. 232, FEBS.

Alan I. Derman et al., "*Escherichia coli* Alkaline Phosphatase Localized to the Cytoplasm Slowly Acquires Enzymatic Activity in Cells Whose Growth Has Been Suspended: a Caution for Gene Fusion Studies", Journal of Bacteriology, Jul. 1995, pp. 3764–3770, vol. 177, No. 13, American Society for Microbiology.

Jan–Olov Höög et al., "Nucleotide sequence of the thioredoxin gene from *Escherichia coli*", Bioscience Reports, 1984, pp. 917–923, vol. 4, The Biochemical Society, Great Britain.

Robert Kuhelj et al., "The preparation of catalytically active human cathepsin B from its precursor expressed in *Escherichia coli* in the form of inclusion bodies", Eur. J. Biochem., 1995, pp. 533–539, vol. 229, FEBS.

Ursula Rinas et al., "Overexpression of Bacterial Hemoglobin Causes Incorporation of Pre–β–Lactamase into Cytoplasmic Inclusion Bodies", Appl. Environ. Microbiol., Feb. 1993, pp. 561–566, vol. 59, No. 2, American Society for Microbiology.

Koen Vandenbroeck et al., "Refolding and single–step purification of porcine interferon–γ from *Escherichia coli* inclusion bodies Conditions for reconstitution of dimeric IFN–γ", Eur.J.Biochem., 1993, pp. 481–486, vol. 215, FEBS.

* cited by examiner

Figure 1b

Complete vector sequences of pTFT74-N1-MCS-H acccgacaccatcgaaattaatacgactcactatagggagaccacaacggtttccctaattgtgagcggataacaatagaaata
attttgtttaactttaagaaggagatatatccatggctgaaactgttgaaagttgtttagcaaaatcccatacagaaaattcatttact
aacgtctggaaagacgacaaaactttagatcgttacgctaactatgagggctgtctgtggaatgctacaggcgttgtagtttgtac
tggtgacgaaactcagtgttacggtacatgggttcctattgggcttgctatccctgaaaatgagggtggtggctctgagggtggc
ggttctgagggtggcggttctccgtacggctctagagtcgacgagctcgatatcggcggccgcgaattctctcatcaccatcac
catcactaagcttcagtcccgggcagtggatccggctgctaacaaagcccgaaaggaagctgagttggctgctgccaccgct
gagcaataactagcataacccccttggggcctctaaacgggtcttgaggggttttttgctgaaaggaggaactatatccggatcg
agatccccacgcgccctgtagcggcgcattaagcgcggcgggtgtggtggttacgcgcagcgtgaccgctacacttgccag
cgccctagcgcccgctcctttcgctttcttcccttcctttctcgccacgttcgccggctttccccgtcaagctctaaatcggggcat
ccctttaggggttccgatttagtgctttacggcacctcgaccccaaaaaacttgattagggtgatggttcacgtagtgggccatcgc
cctgatagacggtttttcgccctttgacgttggagtccacgttctttaatagtggactcttgttccaaactggaacaacactcaaccc
tatctcggtctattcttttgatttataagggattttgccgatttcggcctattggttaaaaaatgagctgatttaacaaaaatttaacgcg
aattttaacaaaatattaacgtttacaatttcaggtggcacttttcggggaaatgtgcgcggaacccctatttgtttatttttctaaata
cattcaaatatgtatccgctcatgagacaataaaccctgataaatgcttcaataatattgaaaaaggaagagtatgagtattcaacat
ttccgtgtcgcccttattcccttttttgcggcattttgccttcctgtttttgctcacccagaaacgctggtgaaagtaaaagatgctga
agatcagttgggtgcacgagtgggttacatcgaactggatctcaacagcggtaagatccttgagagttttcgccccgaagaacg
ttttccaatgatgagcacttttaaagttctgctatgtggcgcggtattatcccgtattgacgccgggcaagagcaactcggtcgcc
gcatacactattctcagaatgacttggttgagtactcaccagtcacagaaaagcatcttacggatggcatgacagtaagagaatt
atgcagtgctgccataaccatgagtgataacactgcggccaacttacttctgacaacgatcggaggaccgaaggagctaaccg
cttttttgcacaacatggggggatcatgtaactcgccttgatcgttgggaaccggagctgaatgaagccataccaaacgacgagc
gtgacaccacgatgcctgtagcaatggcaacaacgttgcgcaaactattaactggcgaactacttactctagcttcccggcaac
aattaatagactggatggaggcggataaagttgcaggaccacttctgcgctcggcccttccggctggctggtttattgctgataa
atctggagccggtgagcgtgggtctcgcggtatcattgcagcactggggccagatggtaagccctcccgtatcgtagttatcta
cacgacggggagtcaggcaactatggatgaacgaaatagacagatcgctgagataggtgcctcactgattaagcattggtaac
tgtcagaccaagtttactcatatatactttagattgatttaaaacttcattttaatttaaaaggatctaggtgaagatcctttttgataat
ctcatgaccaaaatcccttaacgtgagttttcgttccactgagcgtcagaccccgtagaaaagatcaaaggatcttcttgagatcc
ttttttctgcgcgtaatctgctgcttgcaaacaaaaaaaccaccgctaccagcggtggtttgtttgccggatcaagagctaccaa
ctcttttccgaaggtaactggcttcagcagagcgcagataccaaatactgtccttctagtgtagccgtagttaggccaccacttc
aagaactctgtagcaccgcctacatacctcgctctgctaatcctgttaccagtggctgctgccagtggcgataagtcgtgtcttac
cgggttggactcaagacgatagttaccggataaggcgcagcggtcgggctgaacggggggttcgtgcacacagcccagctt
ggagcgaacgacctacaccgaactgagatacctacagcgtgagctatgagaaagcgccacgcttcccgaagggagaaagg
cggacaggtatccggtaagcggcagggtcggaacaggagagcgcacgagggagcttccaggggggaaacgcctggtatctt
tatagtcctgtcgggtttcgccacctctgacttgagcgtcgatttttgtgatgctcgtcaggggggcggagcctatggaaaaacg
ccagcaacgcggcctttttacggttcctggccttttgctggccttttgctcacatg

Figure 2b

Complete vector sequences of pTFT74-H-N1-MCS acccgacaccatcgaaattaatacgactcactatagggagaccacaacggtttccctaattgtgagcggataacaatagaaataattttgt
ttaactttaagaaggagatatatccatggctcatcaccatcaccatcacgaaactgttgaaagttgtttagcaaaatcccatacagaaaatt
catttactaacgtctggaaagacgacaaaactttagatcgttacgctaactatgagggctgtctgtggaatgctacaggcgttgtagtttgt
actggtgacgaaactcagtgttacggtacatgggttcctattgggcttgctatccctgaaaatgagggtggtggctctgagggtggcggt
tctgagggtggcggttcttctagagtcgacgagctcgatatcgaattcggcggccgctaactgactaagcttcagtcccgggcagtgga
tccggctgctaacaaagcccgaaaggaagctgagttggctgctgccaccgctgagcaataactagcataacccttggggcctctaaa
cgggtcttgaggggttttttgctgaaaggaggaactatatccggatcgagatccccacgcgccctgtagcggcgcattaagcgcggcg
ggtgtggtggttacgcgcagcgtgaccgctacacttgccagcgccctagcgcccgctcctttcgctttcttcccttcctttctcgccacgtt
cgccggctttccccgtcaagctctaaatcggggcatccctttagggttccgatttagtgctttacggcacctcgaccccaaaaaacttgatt
agggtgatggttcacgtagtgggccatcgccctgatagacggtttttcgccctttgacgttggagtccacgttctttaatagtggactcttgt
tccaaactggaacaacactcaaccctatctcggtctattcttttgatttataagggattttgccgatttcggcctattggttaaaaaatgagct
gatttaacaaaaatttaacgcgaattttaacaaaatattaacgtttacaatttcaggtggcacttttcggggaaatgtgcgcggaacccctat
ttgtttatttttctaaatacattcaaatatgtatccgctcatgagacaataaaccctgataaatgcttcaataatattgaaaaaggaagagtatga
gtattcaacatttccgtgtcgcccttattcccttttttgcggcattttgccttcctgtttttgctcacccagaaacgctggtgaaagtaaaagat
gctgaagatcagttgggtgcacgagtgggttacatcgaactggatctcaacagcggtaagatccttgagagttttcgccccgaagaacg
ttttccaatgatgagcacttttaaagttctgctatgtggcgcggtattatcccgtattgacgccgggcaagagcaactcggtcgccgcata
cactattctcagaatgacttggttgagtactcaccagtcacagaaaagcatcttacggatggcatgacagtaagagaattatgcagtgctg
ccataaccatgagtgataacactgcggccaacttacttctgacaacgatcggaggaccgaaggagctaaccgcttttttgcacaacatg
ggggatcatgtaactcgccttgatcgttgggaaccggagctgaatgaagccataccaaacgacgagcgtgacaccacgatgcctgta
gcaatggcaacaacgttgcgcaaactattaactggcgaactacttactctagcttcccggcaacaattaatagactggatggaggcgga
taaagttgcaggaccacttctgcgctcggcccttccggctggctggttattgctgataaatctggagccggtgagcgtgggtctcgcgg
tatcattgcagcactggggccagatggtaagccctcccgtatcgtagttatctacacgacggggagtcaggcaactatgatgaacgaa
atagacagatcgctgagataggtgcctcactgattaagcattggtaactgtcagaccaagtttactcatatatactttagattgatttaaaact
tcattttaatttaaaaggatctaggtgaagatcctttttgataatctcatgaccaaaatcccttaacgtgagttttcgttccactgagcgtcag
accccgtagaaaagatcaaaggatcttcttgagatcctttttttctgcgcgtaatctgctgcttgcaaacaaaaaaaccaccgctaccagc
ggtggtttgtttgccggatcaagagctaccaactctttttccgaaggtaactggcttcagcagagcgcagataccaaatactgtccttctag
tgtagccgtagttaggccaccacttcaagaactctgtagcaccgcctacatacctcgctctgctaatcctgttaccagtggctgctgccag
tggcgataagtcgtgtcttaccgggttggactcaagacgatagttaccggataaggcgcagcggtcgggctgaacggggggttcgtg
cacacagcccagcttggagcgaacgacctacaccgaactgagatacctacagcgtgagctatgagaaagcgccacgcttcccgaag
ggagaaaggcggacaggtatccggtaagcggcagggtcggaacaggagagcgcacgagggagcttccaggggggaaacgcctgg
tatctttatagtcctgtcgggtttcgccacctctgacttgagcgtcgattttgtgatgctcgtcaggggggcggagcctatggaaaaacgc
cagcaacgcggcctttttacggttcctggccttttgctggccttttgctcacatg

Figure 5b pBAD-N1-MSC-H Sequence (4357 bp)

```
aagaaaccaattgtccatattgcatcagacattgccgtcactgcgtcttttactggctcttctcgctaaccaaac
cggtaaccccgcttattaaaagcattctgtaacaaagcgggaccaaagccatgacaaaaacgcgtaacaaaagtg
tctataatcacggcagaaaagtccacattgattatttgcacggcgtcacactttgctatgccatagcattttat
ccataagattagcggatcctacctgacgcttttatcgcaactctctactgtttctccatacccgtttttttggg
ctaacaggaggaattaaccatggctgaaactgttgaaagttgtttagcaaaatcccatacagaaaattcatttac
taacgtctggaaagacgacaaaactttagatcgttacgctaactatgagggctgtctgtggaatgctacaggcgt
tgtagtttgtactggtgacgaaactcagtgttacggtacatgggttcctattgggcttgctatccctgaaaatga
gggtggtggctctgagggtggcggttctgagggtggcggttctagagtcgacgagctcgatatcggcggccgcga
attctctcatcaccatcaccatcactaagcttgggcccgaacaaaaactcatctcagaagaggatctgaatagcg
ccgtcgaccatcatcatcatcattgagtttaaacggtctccagcttggctgttttggcggatgagagaagat
tttcagcctgatacagattaaatcagaacgcagaagcggtctgataaaacagaatttgcctggcggcagtagcgc
ggtggtcccacctgacccatgccgaactcagaagtgaaacgccgtagcgccgatggtagtgtggggtctcccca
tgcgagagtagggaactgccaggcatcaaataaaacgaaaggctcagtcgaaagactgggcctttcgttttatct
gttgtttgtcggtgaacgctctcctgagtaggacaaatccgccgggagcggatttgaacgttgcgaagcaacggc
ccggagggtggcgggcaggacgcccgccataaactgccaggcatcaaattaagcagaaggccatcctgacggatg
gcctttttgcgtttctacaaactcttttgtttatttttctaaatacattcaaatatgtatccgctcatgagaca
ataaccctgataaatgcttcaataatattgaaaaaggaagagtatgagtattcaacatttccgtgtcgcccttat
tcccttttttgcggcatttgccttcctgtttttgctcacccagaaacgctggtgaaagtaaaagatgctgaaga
tcagttgggtgcacgagtgggttacatcgaactggatctcaacagcggtaagatccttgagagttttcgccccga
agaacgttttccaatgatgagcacttttaaagttctgctatgtggcgcggtattatcccgtgttgacgccgggca
agagcaactcggtcgccgcatacactattctcagaatgacttggttgagtactcaccagtcacagaaaagcatct
tacggatggcatgacagtaagagaattatgcagtgctgccataaccatgagtgataacactgcggccaacttact
tctgacaacgatcggaggaccgaaggagctaaccgcttttttgcacaacatgggggatcatgtaactcgccttga
tcgttgggaaccggagctgaatgaagccataccaaacgacgagcgtgacaccacgatgcctgtagcaatggcaac
aacgttgcgcaaactattaactggcgaactacttactctagcttcccggcaacaattaatagactggatggaggc
ggataaagttgcaggaccacttctgcgctcggcccttccggctggctggtttattgctgataaatctggagccgg
tgagcgtgggtctcgcggtatcattgcagcactggggccagatggtaagccctcccgtatcgtagttatctacac
gacggggagtcaggcaactatggatgaacgaaatagacagatcgctgagataggtgcctcactgattaagcattg
gtaactgtcagaccaagtttactcatatatactttagattgatttaaaacttcattttaatttaaaaggatcta
ggtgaagatcctttttgataatctcatgaccaaaatcccttaacgtgagttttcgttccactgagcgtcagaccc
cgtagaaaagatcaaaggatcttcttgagatcctttttttctgcgcgtaatctgctgcttgcaaacaaaaaaacc
accgctaccagcggtggtttgtttgccggatcaagagctaccaactctttttccgaaggtaactggcttcagcag
agcgcagataccaaatactgtccttctagtgtagccgtagttaggccaccacttcaagaactctgtagcaccgcc
tacatacctcgctctgctaatcctgttaccagtggctgctgccagtggcgataagtcgtgtcttaccgggttgga
ctcaagacgatagttaccggataaggcgcagcggtcgggctgaacggggggttcgtgcacacagcccagcttgga
gcgaacgacctacaccgaactgagatacctacagcgtgagctatgagaaagcgccacgcttcccgaagggagaaa
ggcggacaggtatccggtaagcggcagggtcggaacaggagagcgcacgagggagcttccaggggaaacgcctg
gtatctttatagtcctgtcgggtttcgccacctctgacttgagcgtcgatttttgtgatgctcgtcaggggggcg
gagcctatggaaaaacgccagcaacgcggcctttttacggttcctggccttttgctggccttttgctcacatgtt
ctttcctgcgttatcccctgattctgtggataaccgtattaccgcctttgagtgagctgataccgctcgccgcag
ccgaacgaccgagcgcagcgagtcagtgagcgaggaagcggaagagcgcctgatgcggtattttctccttacgca
tctgtgcggtatttcacaccgcatatggtgcactctcagtacaatctgctctgatgccgcatagttaagccagta
tacactccgctatcgctacgtgactgggtcatggctgcgccccgacaccgcaacaccgctgacgcgccctga
cgggcttgtctgctcccggcatccgcttacagacaagctgtgaccgtctccgggagctgcatgtgtcagaggttt
tcaccgtcatcaccgaaacgcgcgaggcagcagatcaattcgcgcgcgaaggcgaagcggcatgcataatgtgcc
tgtcaaatggacgaagcagggattctgcaaacccatgctactccgtcaagccgtcaattgtctgattcgttacc
aattatgacaacttgacggctacatcattcacttttcttcacaaccggcacggaactcgctcggggctggcccg
gtgcatttttaaatacccgcgagaaatagagttgatcgtcaaaaccaacattgcgaccgacggtggcgataggc
atccgggtggtgctcaaaagcagcttcgcctggctgatacgttggtcctcgcgccagcttaagacgctaatcct
aactgctggcggaaaagatgtgacagacgcgacggcgacaagcaaacatgctgtgcgacgctggcgatatcaaaa
ttgctgtctgccaggtgatcgctgatgtactgacaagcctcgcgtacccgattatccatcggtggatgagcgat
tcgttaatcgcttccatgcgccgcagtaacaattgctcaagcagatttatcgccagcagctccgaatagcgccct
tcccccttgcccggcgttaatgatttgcccaaacaggtcgctgaaatgcggctggtgcgcttcatccgggcgaaag
aaccccgtattggcaaatattgacggccagttaagccattcatgccagtaggcgcgcggacgaaagtaaacccac
tggtgataccattcgcgagcctccggatgacgaccgtagtgatgaatctctcctggcgggaacagcaaaatatca
cccggtcggcaaacaaattctcgtccctgattttcaccacccctgaccgcgaatggtgagattgagaatataa
ccttcattcccagcggtcggtcgataaaaaaatcgagataaccgttggcctcaatcggcgttaaacccgccacc
agatgggcattaaacgagtatcccggcagcaggggatcattttgcgcttcagccatacttttcatactcccgcca
ttcagag
```

GENERATION OF SPECIFIC BINDING PARTNERS BINDING TO (POLY)PEPTIDES ENCODED BY GENOMIC DNA FRAGMENTS OR ESTS

This application is a Continuation of International application PCT/EP00/06137, filed Jun. 30, 2000 which claims priority to European Patent 99 11 2815.8, filed Jul. 2, 1999.

BACKGROUND

The present invention relates to the generation of specific binding partners binding to (poly)peptides encoded by genomic DNA fragments or ESTs. The (poly)peptides are expressed as part of fusion proteins which are forming inclusion bodies on expression in host cells. The inclusion bodies are used to generate binding partners which bind specifically to said (poly)peptides. The specific binding partners, in particular immunoglobulins or fragments thereof, are useful for analysis and functional characterisation of proteins encoded by nucleic acid sequences comprising the corresponding genomic DNA fragments or ESTs.

The invention further relates to nucleic acid molecules, vectors and host cells to be used in the methods of the present invention.

The invention further relates to the use of fusion proteins comprising the first N-terminal domain of the geneIII protein of filamentous phage as fusion partner for the expression of a (poly)peptide/protein fused to said fusion partner, and to methods for the expression of (poly)peptide/proteins.

Since several years, massive efforts are being undertaken to sequence the human genome, and to identify and characterise structure and function of the proteins encoded therein. Finally, this will lead to novel targets for prevention, diagnosis and therapy of diseases (Collins & Galas, 1993; Adams et al., 1995). Currently, two different approaches are being pursued for identifying and characterising the genes distributed along the human genome. In one approach, large fragments of genomic DNA are isolated, cloned, and sequenced. Potential open reading frames in these genomic sequences are identified using bioinformatics software. However, this approach entails sequencing large stretches of human DNA which do not encode proteins in order to find the protein encoding sequences scattered throughout the genome. In addition to requiring extensive sequencing, the bioinformatics software may mischaracterize the genomic sequences obtained. Thus, the software may produce false positives in which non-coding DNA is mischaracterised as coding DNA or false negatives in which coding DNA is mislabelled as non-coding DNA.

In an alternative approach, complementary DNAs (cDNAs) are synthesised from isolated messenger RNAs (mRNAs) which encode human proteins. Using this approach, sequencing is only performed on DNA which is derived from protein coding sequences of the genome. Often, only short stretches of the cDNAs are sequenced to obtain sequences called expressed sequence tags (ESTs) (WO93/00353). In principle, the ESTs may then be used to isolate or purify extended cDNAs which include sequences adjacent to the EST sequences. These extended cDNAs may contain portions or the full coding sequence of the gene from which the EST was derived.

By analysing the genomic DNA or fragments thereof, ESTs, extended cDNAs, and/or the (poly)peptides/proteins encoded thereby, in certain cases, where homology, structural motifs etc. can be identified, it may be possible to assign a function to the (poly)peptide/protein which can be tested or verified in vitro or in vivo. However, the various EST-sequencing efforts have led to enormous numbers of ESTs, and to the problem how best to structure that information and how to identify interesting sequences. Hence, there is still a need for developing and using research tools directed against the (poly)peptide/protein of interest to analyse their localisation on cell and tissue types, their up- or down-regulation in certain disease or development stages or their role in activating or blocking certain interactions or signalling routes. One approach is to use antibodies or fragments thereof as such research tools. In WO93/00353 it was suggested to express the ESTs and to generate antibodies by immunising animals with the corresponding (poly) peptides. In a similar approach, DNA constructs comprising EST sequences have been injected into animals to generate an immune response against the (poly)peptide expressed in vivo (Sykes & Johnston, 1999). However, these approaches are not amenable to a high-throughput generation of antibodies. Alternatively, antibodies are generated against sets of overlapping peptides covering the EST sequence (Persic et al., 1999). In combination with screening recombinant antibody libraries, this approach can in principle be developed to generate antibody fragments as research tools with high throughput. However, it is often difficult to obtain anti-peptide antibodies with sufficiently high affinities.

Thus the technical problem underlying the present invention is to provide a generally applicable method for the generation of specific binding partners binding to (poly) peptides encoded by genomic DNA fragments or by ESTs, especially of antibodies or antibody fragments, for analysis aid functional characterisation of proteins corresponding to genomic DNA or ESTs. The solution to the above technical problem is achieved by providing the embodiments characterised in the claims. The technical approach of the present invention, to provide (poly)peptides encoded by genomic DNA fragments or ESTs for the generation of specific binding partners, such as antibodies or antibody-derived products, by expressing the (poly)peptides as fusions with (poly)peptide/protein fusion partners which lead to the formation of inclusion bodies on expression in host cells, such as E. coli, and to generate specific binding partners against the inclusion bodies and fusion proteins, obtainable therefrom, is neither provided nor suggested by the prior art.

A further problem related to the present invention was to devise a method for the expression of (poly)peptide/proteins which are not easily expressed in free form, e.g. since they are toxic to the host cell. The solution to that technical problem is also achieved by providing the embodiments characterised in the claims. The technical approach of the present invention, express the (poly)peptide/proteins as fusion proteins comprising the first N-terminal domain of the geneIII protein of filamentous phage leading to the formation of inclusion bodies, is neither provided nor suggested by the prior art.

SUMMARY

Thus, the present invention relates to a method for generating a specific binding partner to a (poly)peptide which is encoded by a nucleic acid sequence comprised in a genomic DNA fragment or an expressed sequence tag (EST) comprising:

a) expressing a nucleic acid molecule encoding a fusion protein in a host cell under conditions that allow the formation of inclusion bodies comprising said fusion protein, wherein said fusion protein comprises aa) a (poly)peptide/protein fusion partner which is deposited in inclusion bodies when expressed in said host cell under said conditions and ab) said (poly)peptide;

b) isolating said inclusion bodies; and c) generating a specific binding partner that binds specifically to said (poly)peptide.

DETAILED DESCRIPTION

In the context of the present invention, a "specific binding partner" is a molecule which is able to specifically bind to a (poly)peptide of interest. Such a specific binding partner may be a peptide, a constrained peptide, an immunoglobulin or fragment thereof, or a cognate binding partner of a naturally occurring protein, e.g. a ligand to a receptor which comprises the (poly)peptide of interest. Such cognate ligand may be obtainable by screening a cDNA expression library for binding to the fusion protein of the present invention. The specific binding partner may also be a non-proteinaceous specific binding partner such as a small molecule, e.g. obtainable by screening of a combinatorial library of small molecules. A specific binding partner may further be modified to enable the detection of an interaction of a specific binding partner and the corresponding (poly)peptide. Such modification may be a detection and/or purification tag (Hochuli et al., 1988; Lindner et al., 1992; Hopp et al., 1988; Prickett et al., 1989; Knappik & Plückthun, 1994), or an enzyme (Blake et al., 1984) or a reporter molecule fused or coupled to the specific binding partner. In the context of the present invention, the term "(poly) peptide" relates to molecules consisting of one or more chains of multiple, i.e. two or more, amino acids linked via peptide bonds. The term "protein" refers to (poly)peptides where at least part of the (poly)peptide has or is able to acquire a defined three-dimensional arrangement by forming secondary, tertiary, or quaternary structures within and/or between its (poly)peptide chain(s). This definition comprises proteins such as naturally occurring or at least partially artificial proteins, as well as fragments or domains of whole proteins, as long as these fragments or domains have a defined three-dimensional arrangement as described above. The term "genomic DNA fragment" refers to a contiguous nucleic acid sequence forming part of the genome of an organism and being obtained or obtainable therefrom. The term "expressed sequence tags (ESTs)" are contiguous DNA sequences obtained by sequencing stretches of cDNAs. According to the present invention, such a genomic DNA fragment or EST comprises a nucleic acid sequence which encodes a (poly)peptide or consists of a putative open reading frame (ORF). The EST databases (Eckmann et al., 1998; Bouck et al., 1999) often contain sequences of low sequence quality (Aaronson et al., 1996). One of ordinary skill in the art will be able to identify at least one putative ORFs in a given genomic DNA fragment or EST sequence, and it will not constitute an undue burden for the person skilled in the art to clone all ORFs identified in that way for the expression of a corresponding set of said fusion proteins, and to use them according to the present invention. The length of the genomic DNA fragment or EST is preferably between 100 and 2000 base pairs, more preferably between 200 and 1500 base pairs. The nucleic acid molecule encoding a fusion protein used according to the present invention, or an appropriate vector comprising said nucleic acid molecule, further comprises non-coding DNA sequences which are required to cause or allow the expression of the fusion protein. Methods for construction of nucleic acid molecules encoding a fusion protein used according to the present invention, for construction of vectors comprising said nucleic acid molecules, for introduction of said vectors into appropriately chosen host cells, for causing or achieving the expression of said fusion proteins are well-known in the art (see, e.g., Sambrook et al., 1989; Ausubel et al., 1994). The formation of inclusion bodies can be observed in several host systems in the course of the expression of a (poly) peptide/protein. Inclusion bodies are insoluble aggregates of (poly)peptide/protein deposited within a host cell. They are very dense particles which exhibit an amorphous or paracrystalline structure independent of their subcellular location. Under appropriate conditions the recombinant (poly)peptide/protein deposited in inclusion bodies amounts to about 50% or more of the total cell protein. The formation of inclusion bodies, and their properties, and applications thereof have been investigated in detail (see, for example, Rudolph, 1996; Rudolph & Lilie, 1996; Rudolph et al., 1997; Lilie et al., 1998). Methods of purifying inclusion bodies have been described therein as well and are well-known to one of ordinary skill in the art. The use of inclusion body formation by expression of fusion proteins comprising a fusion partner and a (poly)peptide/protein as a general means of expressing said (poly)peptide/protein has been described (WO 98/30684). A fusion partner suitable for a method according to the present invention may be any (poly)peptide/protein which can be found in inclusion bodies when expression in a host cell. In most cases, inclusion body formation is a consequence of high expression rates, regardless of the system or protein used. There seems to be no correlation between the propensity of inclusion body formation of a certain protein and its intrinsic properties, such as molecular weight, hydrophobicity, folding pathways, and so on. (Poly)peptides/proteins where inclusion body formation has been observed and which, therefore, are suitable candidates to be used as fusion partners according to the present invention, include, but are not limited to, *E. coli* proteins such as maltose-binding protein (Betton & Hofnung, 1996), RNAse II (Coburn & Mackie, 1996), alkaline phosphatase (Derman & Beckwith, 1995), phosholipase A (Dekker et al., 1995), β-lactamase (Rinas & Bailey, 1993), thioredoxin (Hoog, et al., 1984; WO 98/30684), and non *E. coli* proteins such as human procathepsin B (Kuhelj et al., 1995), porcine interferon-γ (Vandenbroeck et al., 1993), or T5 DNA polymerase (Chatterjee et al., 1991). The host referred to above may be any of a number commonly used in the production of proteins, including but not limited to bacteria, such as *E. coli* (see. e.g., Ge et al, 1995) or *Bacillus subtilis* (Wu et al., 1993); fungi, such as yeasts (Horwitz et al., 1988; Ridder et al., 1995) or filamentous fungus (Nyyssönen et al., 1993); plant cells (Hiatt, 1990, Hiatt & Ma, 1993; Whitelam et al., 1994), insect cells (Potter et al., 1993; Ward et al., 1995), or mammalian cells (Trill et al., 1995).

The generation, and optionally, identification, of "a binding partner that binds specifically to said (poly)peptide" can be achieved by using a variety of methods, depending on the type of specific binding partner, which are well-known to one of ordinary skill in the art. For example, combinatorial libraries of chemical compounds, peptides or biomolecules, such as immunoglobulins, can be screened and/or selected against the isolated inclusion body as target, preferably after purification, or, more preferably, against the fusion protein obtained from said inclusion bodies, either in solubilised or in refolded form, or against the free (poly)peptide as target (see, for example: Pinilla et al., 1999; Woodbury & Venton, 1999; Borman, 1999; Eisele et al., 1999; Lebl, 1999).

In a preferred embodiment of the method of the invention, said fusion protein comprises said fusion partner as N-terminal portion and said (poly)peptide as C-terminal portion. Further preferred is a method, wherein said fusion protein further comprises a (poly)peptide linker linking said fusion partner and said (poly)peptide. The linker may consist of about 1 to about 30, preferably of between about 5 and about 15 amino acids. Particularly preferred is a method, wherein, said linker comprises a cleavage signal. In the context of the present invention, the term "cleavage signal" refers to a amino acid sequences which allows to cleave, e.g. by chemical or enzymatic reactions, the fusion protein between said fusion partner and said (poly)peptide to be able to obtain said (poly)peptide in free form. Such cleavage signal is preferably a specific recognition sequence of a protease well known to one of ordinary skill in the art, such as enterokinase or thrombin. Alternatively, the fusion protein might be cleaved by chemical cleavage with a chemical such as cyanogen bromide.

Said fusion protein may further comprise additional (poly)peptide sequences at N- and/or C-terminus, and/or in said (poly)peptide linker. This comprises, for example, (poly)peptides which allow to identify and/or purify said fusion protein. Examples for such (poly)peptide tags are $His_n$ (Hochuli et al., 1988; Lindner et al., 1992), myc, FLAG (Hopp et al., 1988; Prickett et al., 1989; Knappik & Pl ückthun, 1994), or a Strep-tag (Schmidt & Skerra, 1993; Schmidt & Skerra, 1994; Schmidt et al., 1996). These tags are all well known in the art and are fully available to the person skilled in the art.

In a yet further preferred embodiment of the method of the invention, said genomic DNA fragment or said EST is obtained from a prokaryotic organism or from a virus. Most preferred is a method wherein said prokaryotic organism or virus is a pathogen.

By sequencing the genome of organisms pathogenic to human, or pathogenic to animals or plants, new proteinaceous targets for prevention, diagnosis and/or therapeutic intervention are being sought.

Further preferred is a method wherein said nucleic acid is expressed under conditions allowing over-expression of said fusion protein.

In a further preferred embodiment, the invention relates to a method wherein said genomic DNA fragment or said EST is obtained from a eukaryotic organism.

In a preferred embodiment, the present invention relates to a method wherein said genomic DNA fragment or said EST is obtained from a non-mammalian species.

Further preferred is a method wherein said genomic DNA fragment or said EST is obtained from a mammalian species.

In a most preferred embodiment the present invention relates to a method wherein said mammalian species is human.

In a preferred embodiment of the method of the invention, said host cell is a eukaryotic cell. Particularly preferred is a yeast or insect cell.

In a most preferred embodiment of the method of the invention, said host cell is a prokaryotic cell. Particularly preferred is a bacterial cell. Most preferably, said bacterial cell is an *E. coli* cell.

An additional preferred embodiment of the invention relates to a method wherein said fusion protein is expressed in the cytosol of a bacterial host cell. Particularly preferred is the cytosolic expression of fusion proteins according to the present invention wherein said fusion partner contains at least one disulfide bond. It has been found that inclusion body formation can be anticipated if a disulfide bonded (poly)peptide/protein is produced in the bacterial cytosol, as formation of disulfide bonds does usually not occur in this reducing cellular compartment. The consequence is improper folding resulting in aggregation (Lilie et al., 1998).

Further preferred is a method where said fusion partner is a secreted protein, and wherein said nucleic acid does not comprise a nucleic acid sequence encoding a signal sequence for the transport of the fusion protein to the periplasm. It has been observed that cytosolic expression of secreted (poly)peptide/protein leads to the formation of inclusion bodies (Lilie et al., 1998).

In a preferred embodiment the present invention relates to a method wherein said fusion partner is an endogenous (poly)peptide/protein of said host cell.

Most preferred is a method wherein said fusion partner is a (poly)peptide/protein foreign to said host cell. Particularly preferred is a method wherein said fusion partner is taken from the list of *E. Coli* maltose-binding protein, *E. coli* RNAse II, *E. coli* alkaline phosphatase, *E. coli* phosholipase A, *E. coli* β-lactamase, *E. coli* thioredoxin, human procathepsin B, porcine interferon, and T5 DNA polymerase.

In a further most preferred embodiment of the method of the invention, said host cell is *E. coli* and said fusion partner comprises the first N-terminal domain of the geneIII protein of a filamentous phage. Preferably, said fusion partner consists of the two N-terminal domains of the geneIII protein, more preferably of the first N-terminal domain of the geneIII protein. Most preferably, said fusion partner consists of amino acids 1 to 82 of the geneIII protein.

Infection of *Escherichia coli* by the Ff filamentous phages f1, fd, and M13 is initiated by interaction of the geneIII protein (g3p) located at one end of the phage particle with the tip of the F conjugative pilus (Model & Russel, 1988). Mature g3p (406 amino acids) consists of 3 domains separated by linker sequences (Stengele et al., 1990; Krebber et al., 1997). The following roles could be assigned to the individual domains: The N-terminal domain of g3p (N1) is responsible for membrane penetration (Riechmann & Holliger, 1997), the middle domain (N2) for binding of the bacterial F-pilus (Stengele et al., 1990) and the C-terminal domain (CT) plays a role in phage morphogenesis and caps one end of the phage particle (Crissman & Smith, 1984). The crystal structure of the two N-terminal domains of g3p (N1-N2) and the solution structure of N1 have been solved (Lubkowski et al., 1998; Holliger & Riechmann, 1997). Purified N1 was shown to be highly soluble and monomeric at mM concentrations (Holliger & Riechmann, 1997). Expression of N1 or N1-N2 in the cytoplasm of *E. coli*, however, leads to the formation of inclusion bodies from which the proteins can be refolded (C. Krebber, 1996; Krebber et al., 1997). Since expression of N1 and N1-N2fusion proteins are toxic to the cells (C. Krebber, 1996), tight regulation of transcription of the fusion genes are preferred using for example the pET (Stratagene, La Jolla, Calif., USA) or the pBAD expression system (Invitrogen BV, Groningen, The Netherlands). The use of these vectors is in all cases applicable where toxic effects of gene products is being expected, assumed or observed, and is one of the first steps well known to one of ordinary skill in the art in adjusting expression conditions. Fusion partners comprising the first N-terminal domain of guIIIp are particularly useful since the fusion protein readily form inclusion bodies on cytosolic expression, but are easily solubilised (Krebber et al., 1997). The fusion partner may also be a variant or a mutant of a parental fusion partner referred to hereinabove (such as a (poly)peptide/protein comprising the first N-terminal domain of gIIIp), provided that such variant or mutant is deposited in inclusion bodies as well when expressed in host cell under conditions where the parental fusion partner is deposited in inclusion bodies. Such variant or mutant may result from the parental fusion partner e.g. by adding, substituting and/or deleting one or more amino acid residue(s). Since the formation of inclusion bodies on expression is a property which can easily be monitored by one of ordinary skill in the art, it does not require an undue burden of experimentation to identify variants or mutants with properties suitable for the methods of the present invention.

In a further preferred embodiment, the invention relates to a method wherein step b) further comprises the step of (i) solubilising said fusion protein under suitable conditions. In a yet further preferred embodiment, the present invention relates to a method wherein step b) further comprises the step of (ii) refolding said fusion protein under suitable conditions.

Methods for solubilising and/or refolding (poly)peptides/proteins found deposited in inclusion bodies have been thoroughly investigated and are well known to the practitioner of ordinary skill in the art (see, for example, Rudolph, 1996; Rudolph & Lilie, 1996; Rudolph et al., 1997; Lilie et al., 1998).

In another preferred embodiment, the invention relates to a method wherein said fusion protein further comprises a (poly)peptide linker linking said fusion partner and said (poly)peptide, wherein said linker comprises a cleavage signal, and wherein step b) further comprises the steps of (iii) cleaving said fusion protein between said fusion partner and said (poly)peptide, and (iv) isolating said (poly)peptide in free form. Further preferred is a method further comprising the step of purifying said fusion protein or said (poly)peptide in free form.

The construction of fusion proteins comprising a cleavage signal which allows to cleave the fusion protein between said fusion partner and said (poly)peptide has been described hereinabove.

In a preferred embodiment of the method of the invention, said specific binding partner is an immunoglobulin or a fragment thereof In this context, "immunoglobulin" is used as a synonym for "antibody". Immunoglobulin fragments according to the present invention may be Fv (Skerra & Plückthun, 1988), scFv (Bird et al., 1988; Huston et al., 1988), disulfide-linked Fv (Glockshuber et al., 1992; Brinkmann et al., 1993), Fab, (Fab')2 fragments or other fragments well-known to the practitioner skilled in the art, which comprise the variable domain of an immunoglobulin or immunoglobulin fragment. Particularly preferred is the scFv fragment format.

In a most preferred embodiment of the method of the invention, said immunoglobulin or fragment thereof is generated by (i) immunisation of an animal with said inclusion bodies, said fusion protein or said (poly)peptide, and (ii) by selecting an immunoglobulin produced by said animal which specifically binds to said inclusion bodies, said fusion protein or said (poly)peptide. Methods for immunising animals and for screening and/or selection of specific immunoglobulin are well-known to one of ordinary skill in the art.

In a further most preferred embodiment of the method of the invention, said immunoglobulin or fragment thereof is generated by selecting a member of a recombinant library of immunoglobulins or fragments thereof which specifically binds to said inclusion bodies, said fusion protein or said (poly)peptide. Recombinant libraries of immunoglobulins or fragments thereof have been described in various publications (see, e.g., Vaughan et al., 1996; Knappik et al., 2000; WO 97/08320), and are well-known to one of ordinary skill in the art.

Particularly preferred is a method wherein said library is displayed on the surface of a replicable genetic package.

The term "replicable genetic package" refers to an entity which combines phenotype and genotype of members of a library of (poly)peptides/proteins by linking the genetic information encoding the library member and the (poly)peptide/protein expressed therefrom. The library can be screened and/or selected for a desired property, and the (poly)peptide/protein being screened and/or selected can be identified via the genetic information associated with the same. Examples for "replicable genetic packages" comprise cells, such as bacteria (WO 90/02809; Georgiou et al., 1993; Francisco & Georgiou, 1994; Daugherty et al., 1998), yeast (Boder & Wittrup, 1997; Kieke et al., 1997; Cho et al., 1998; Kieke et al., 1999) insect cells (Ernst et al., 1998), viruses, such as bacteriophage (WO 90/02809; Kay et al., 1996; Dunn, 1996; McGregor, 1996) retroviruses (Russell et al., 1993), spores (WO 90/02809), or complexes of nucleic acid molecules and (poly)peptides/proteins expressed therefrom, such as in ribosome complexes (Hanes & Plückthun, 1997; Hanes et al., 1998; Hanes et al., 1999) or in complexes connected either non-covalently (Cull et al., 1992; Schatz, 1993; Schatz et al., 1996; Gates et al., 1996) or covalently (Nemoto et al., 1997).

Further preferred is a method wherein said replicable genetic package is a filamentous phage.

In the context of the present invention, the term "filamentous phage" refers to a class of bacteriophage which are able to infect a variety of Gram negative bacteria. They have a single-stranded, covalently closed DNA genome which is packaged in a protein coat forming a long cylinder. The best characterised of these phage are M13, fd, and fl and derivatives thereof. Filamentous phage have been used extensively for the display of foreign (poly)peptides/proteins and libraries thereof, and the various approaches and applications have been reviewed in several publications (e.g. Kay et al., 1996; Dunn, 1996; McGregor, 1996).

Particularly preferred is the use of a fusion protein comprising the N-terminal domain of the geneIII protein (g3p) of filamentous phage as fusion partner for biopanning of a recombinant library of immunoglobulins or fragments thereof displayed on the surface of filamentous phage. The following properties of N1 make it an especially suitable candidate to be used in biopanning of phage display libraries:

N1 (amino acids 1–82 of the mature g3p) is small and has a low pI of 4.14, which is advantageous for coating to conventional micro titer plates used for biopanning which is routinely done at physiological pH most phages displaying N1-binding scFvs on their surface should automatically be removed since they should bind to other phages which carry 3–5 copies of g3p comprising N1 on their surface.

In another embodiment, the present invention relates to a nucleic acid molecule encoding a fusion protein comprising aa) the first N-terminal domain of the geneIII protein of filamentous phage and ab) a (poly)peptide which is encoded by a nucleic acid sequence comprised in a genomic DNA fragment or an expressed sequence tag (EST), wherein said nucleic acid molecule does not comprise a nucleic acid sequence encoding a signal sequence for the transport of the fusion protein to the periplasm of a bacterial host cell.

In a further embodiment, the invention relates to a vector which comprises a nucleic acid molecule of the present invention.

Preferably, said vector is an expression vector.

In another embodiment, the invention relates to a host cell comprising a nucleic acid or a vector according to the present invention.

Particularly preferred is a host cell which is an *E. coli* cell.

Additionally, the invention relates to the use of a fusion protein comprising the first N-terminal domain of the geneIII protein of filamentous phage as fusion partner for the expression of a (poly)peptide/protein fused to said fusion partner, wherein said fusion protein is obtained in the form of inclusion bodies. The general method of using inclusion body formation formed by expression of fusion proteins comprising a fusion partner and a (poly)peptide/protein as a means of expressing said (poly)peptide/protein has been described (WO 98/30684). The fusion protein may further comprise a linker sequence linking said fusion partner and said (poly)peptide/protein. The linker may consist of about 1 to about 30, preferably of between about 5 and about 15 amino acids. The linker may comprise a cleavage signal which allows to cleave the fusion protein between the fusion partner and the (poly)peptide/protein to be able to obtain said (poly)peptide/protein in free form. Such cleavage signal is preferably a specific recognition sequence of a proteases well known to one of ordinary skill in the art, such as enterokinase or thrombin. Alternatively, the fusion protein might be cleaved by chemical cleavage with a chemical such as cyanogen bromide. Such fusion proteins, after refolding, can be used in in vitro SIP as well (Krebber et al., 1997).

The invention furthermore relates to a method for the expression of a (poly)peptide/protein comprising:

a) expressing a nucleic acid molecule encoding a fusion protein in a host cell under conditions that allow the formation of inclusion bodies comprising said fusion protein, wherein said fusion protein comprises aa) the first N-terminal domain of the geneIII protein of filamentous phage, and ab) said (poly)peptide/protein.

Particularly preferred is a method further comprising the steps of b) isolating said inclusion bodies, and c) solubilising said fusion protein under suitable conditions.

The specific binding partners generated according to the present invention may be used for the identification and/or characterisation of a naturally occurring (poly)peptide/protein comprising said (poly)peptide. Such uses include, but are not limited to, the use of specific binding partners such as immunoglobulins or fragments thereof in immunoassays such as ELISA, in Western blot analysis of cell extracts, immunohistochemistry or immunocytochemistry on tissues or cells, immunoprecipitations, immunocoprecipitation using cell extracts, and so on. The use of specific binding partners such as immunoglobulins or fragments thereof in such binding assays, or in similar methods, and in the isolation of target material is well-known to one of ordinary skill in the art.

By using the specific binding partner generated according to the present invention it will be possible to identify and/or characterise naturally occurring (poly)peptide/protein comprising said (poly)peptide. Methods for isolating naturally occurring (poly)peptides/proteins from natural sources, and methods for the identification of these (poly)peptide/protein, either directly or via the genetic information encoding these (poly)peptide/protein, are well-known to one of ordinary skill in the art.

DRAWINGS

FIG. 1: (A) Vector map of expression vector pTFT74-N1-MCS-H. (B) Sequence of expression vector pTFT74-N1-MCS-H. (SEQ ID NO:8)

Figure 2A:
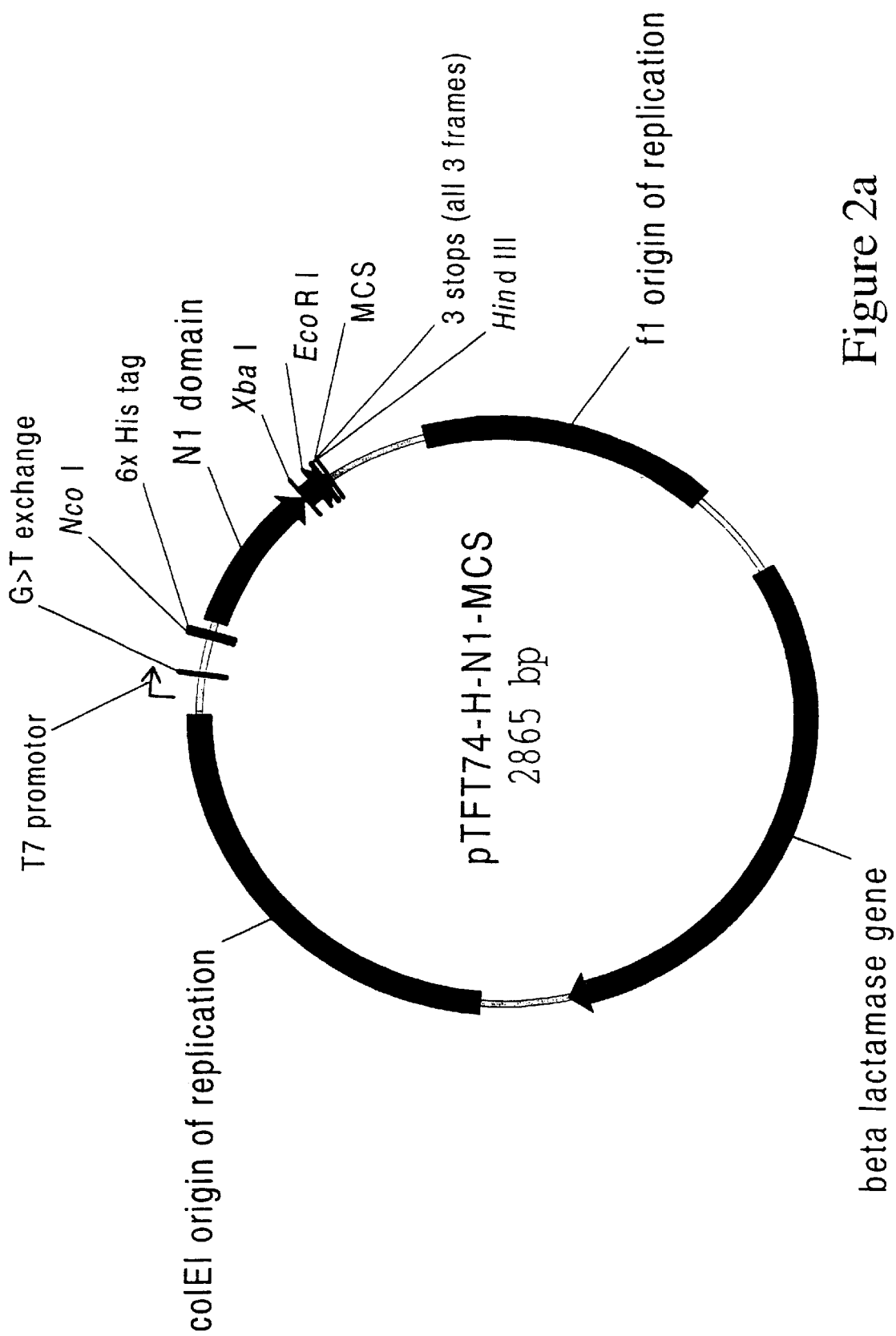

FIG. 2: (A) Vector map of expression vector pTFT74-H-N1-MCS. (B) Sequence of expression vector pTFT74-H-N1-MCS. (SEQ ID NO:9)

Figure 3:
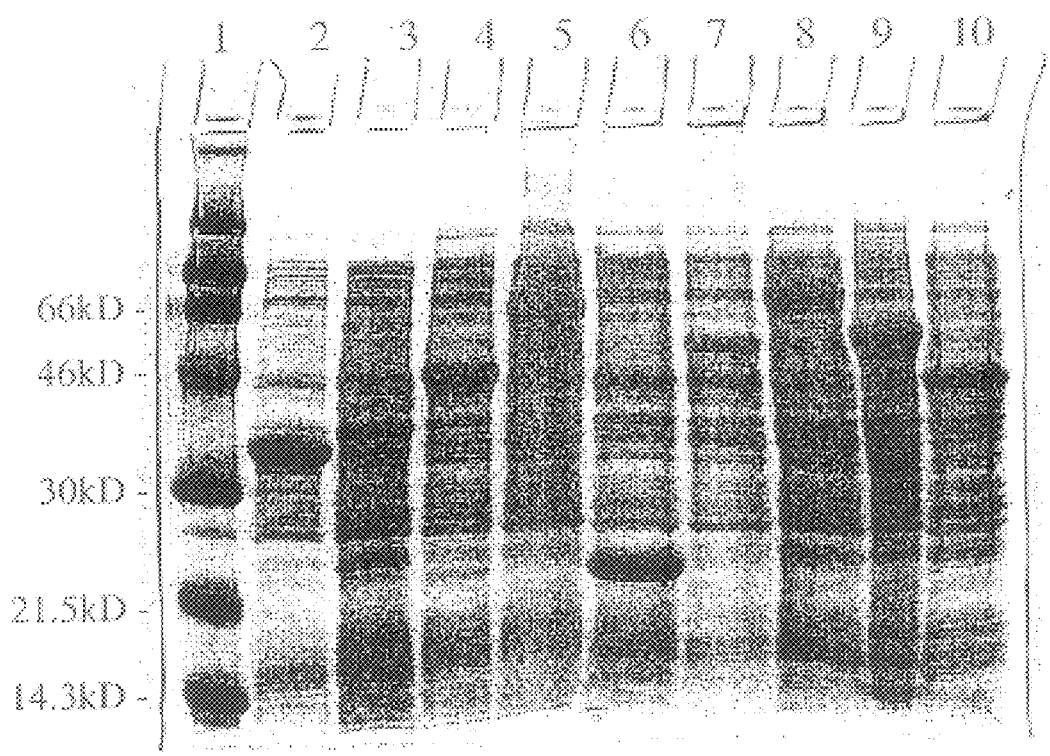

FIG. 3: Expression of fusion protein constructs After expression, whole cell lysates were run on a 12% SDS PAA Ready gel (Bio-Rad) under reducing conditions. The gel was stained using Coomassie Blue. Lane1, High molecular weight Rainbow marker (Amersham), molecular masses of proteins are indicated; lane 2, N1 fused to a fragment of an MHC classII beta chain (calculated mass of fusion protein: 33.4 kD), lane 3, N1 fused to a fragment of an MHC classII alpha chain (calculated mass of fusion protein: 32.2 kD); lane 4, N1 fused to the very C-terminal 280 amino acids of human NF-κB p100 amplified by PCR for cloning into pTFT74-N1-MCS-H from IMAGE clone 434322 (calculated mass of fusion protein: 39.9 kD); lane 5, N1 fused to mature human ICAM-1 (calculated mass of fusion protein: 65.7 kD); lane 6, N1 fused to a fragment of human ICAM-1 (amino acids 401–480 of the unprocessed protein, calculated mass of fusion protein: 19.3 kD); lane 7, N1 fused to a fragment of human ICAM-1 (amino acids 151–532 of the unprocessed protein, calculated mass of fusion protein: 52.2 kD); lane 8, N1 fused to a fragment of UL84 of human cytomegalovirus (amino acids 68–586, calculated mass of fusion protein: 68.4 kD); lane 9, N1 fused to a fragment of UL84 of human cytomegalovirus (amino acids 200–586, calculated mass of fusion protein: 53.2 kD); and lane 10, N1 fused to a fragment of UL84 of human cytomegalovirus (amino acids 300–586, calculated mass of fusion protein: 42.2 kD)

Figure 4:
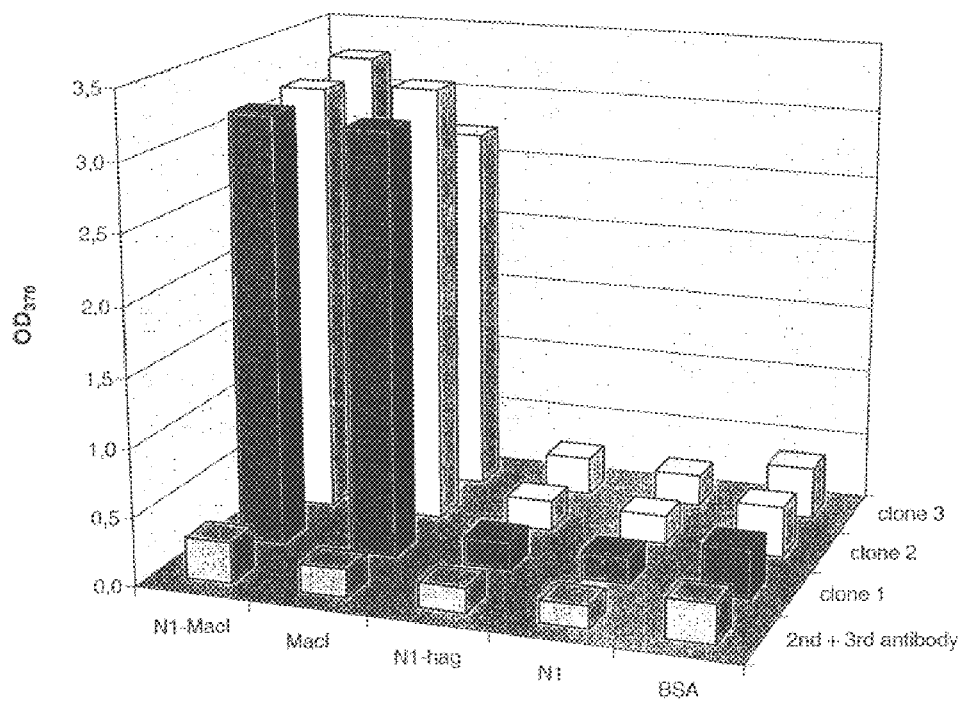

FIG. 4: Specificity ELISA of 3 different svFvs (clones 1–3) selected against N1-MacI. Preparation of the periplasmic fraction of JM83 cells containing scFv clones 1–3 on an expression vector was as described (Knappik et al., 1993). 1 μg of N1-MacI, MacI, N1-hag, N1 and BSA, respectively, in PBS was coated for 12 h at 4° C. to a Nunc Maxisorb microtiter plate (# 442404) which was then blocked for 2 h at room temperature using PBS containing 5% skim milk powder. Periplasmic fractions were mixed 1:1 with PBS containing 5% skim milk powder and 0.05% Tween 20 and incubated for 1h at room temperature before they were added to the blocked wells of the microtiter plate. Incubation was 1 h at room temperature. Since all HuCAL scFvs carry an N-terminal M1 FLAG (Knappik & Plückthun, 1994), an M1 anti-FLAG antibody (Sigma # F-3040) was applied to the wells and incubated for 1 h at room temperature ($2^{nd}$ antibody). Bound M1 anti-FLAG antibodies were detected with an anti-mouse IgG-HRP conjugate (Sigma # A-6782; $3^{rd}$ antibody) and BM blue soluble (Boehringer Mannheim # 1484281) as substrate. After blocking and incubation with the periplasmic fractions, the M1 anti-FLAG antibody and the anti-mouse IgG-HRP conjugate, the ELISA plate was washed 5 times using TBS buffer containing 0.05% Tween 20 and 1 mM $CaCl_2$. Absorbance at 370 nm was measured after-addition of substrate.

Figure 5A:
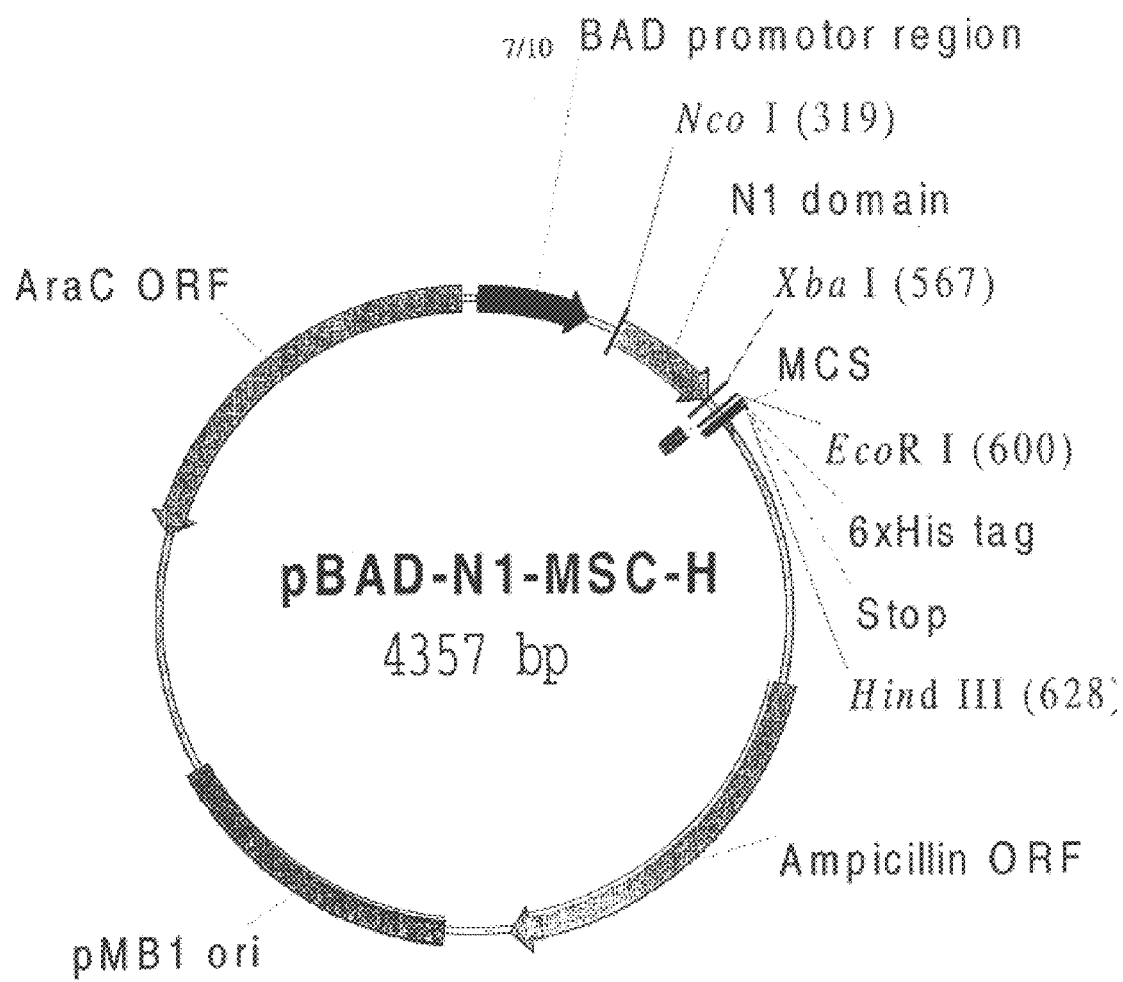

FIG. 5: (A) Vector map of expression vector pBAD-N1-MCS-H. (B) Sequence of expression vector pBAD-N1-MCS-H. (SEQ ID NO:10)

Figure 6:
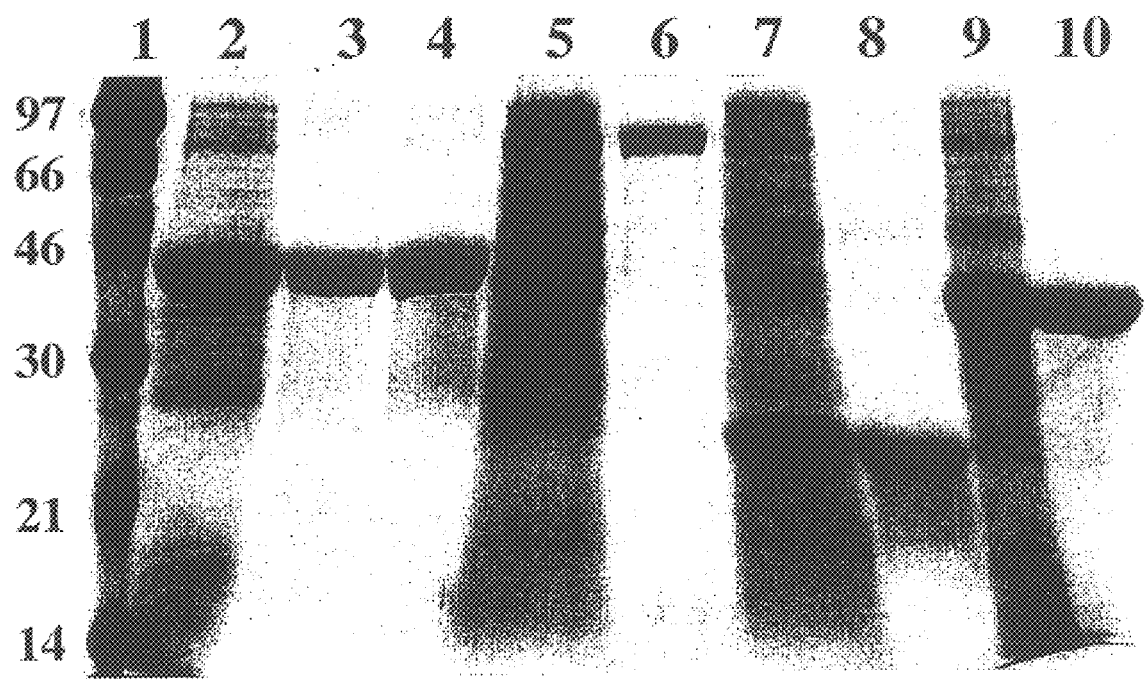

FIG. 6: Expression of fusion protein constructs and one step affinity purification. Samples were run on a 12% SDS polyacryamide gel (Bio-Rad) under reducing conditions. The gel was stained using Coomassie Blue. Lane 1, marker proteins with relative molecular masses indicated (to be multiplied by 103); lane 2, crude lysate of *E. coli* BL21 (DE3)pLysS harbouring vector pTFT74-N1-MacI after 3 h induction with 1 mM IPTG; lane 3, refolded inclusion bodies from N1-MacI expression; lane 4, affinity-purified, refolded N1-MacI; lane 5, crude lysate of *E. coli* BL21 (DE3)(pLysS) harbouring vector pTFT74-N1-U2 after 3 h induction with 1 mM IPTG; lane 6, affinity-purified, refolded N1-U2; lane 7, crude lysate of *E. coli* BL21(DE3) (pLysS) harbouring vector pTFT74-N1-I3 after 3 h induction with 1 mM IPTG; lane 8, affinity-purified, refolded N1-I3; lane 9, crude lysate of *E. coli* BL21(DE3)(pLysS) harbouring vector pTFT74-N1-B1 after 3 h induction with 1 mM IPTG; lane 10, affinity-purified, refolded N 1-B1.

Figure 7:
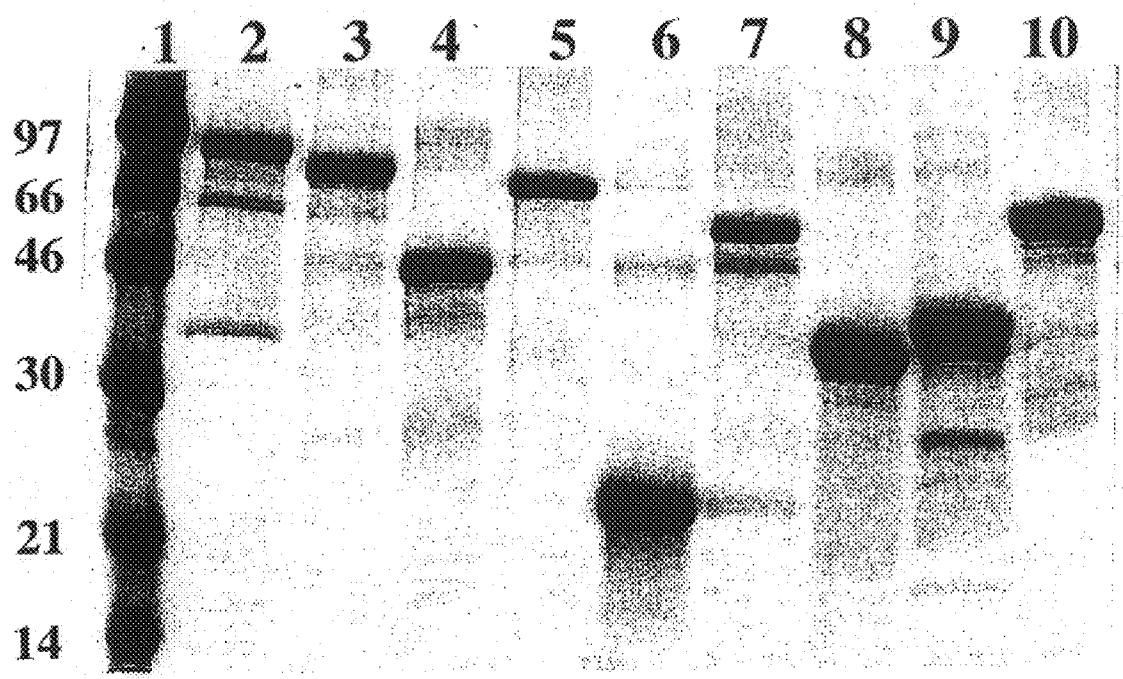

FIG. 7: Purity of affinity purified, refolded N1-fusion proteins. Samples were run on a 12% SDS polyacryamide gel (Bio-Rad) under reducing conditions. The gel was stained using Coomassie Blue. The calculated molecular weight of the fusion protein is given in brackets. Lane 1, marker proteins with relative molecular masses indicated (to be multiplied by 103); lane 2, N1-U1fl (75.6 kDa); lane 3, N1-U2 (68.4 kDa); lane 4, N1-U4 (42.2 kDa); lane 5, N1-I1fl (65.7 kDa); lane 6, N1-I3 (19.3 kDa); lane 7, N1-I4 (52.2 kDa); lane 8, N1-B1 (33.4 kDa); lane 9, N1-A14 (32.2 kDa); lane 10, N1-Np50 (51.3 kDa).

The example illustrates the invention

EXAMPLES

In the following description, all molecular biology experiments are performed according to standard protocols (Ausubel et al., 1995).

Example 1

Functional Genomics with Phages: Overexpression of N1 Fusion Proteins, Purification from Inclusion Bodies and Biopanning of Phage Display Libraries Against the Refolded Fusion Proteins Generation of Expression Vectors All vectors used are derivatives of expression vector pTFT74 (Freund et al., 1993). Into this vector, the DNA sequence coding for amino acids 1–82 of mature g3p of phage fd containing an additional methionine residue at the N-terminus, a multiple cloning site and a DNA sequence coding for a 6×His purification tag has been inserted between the unique NcoI and HindIII sites generating vector pTFT74-N1-MCS-H (FIG. 1, complete vector sequence given in appendix). The first 82 amino acids of the mature g3p contain domain N1 (amino acids 1–67) and the first 15 amino acids of the linker between N1 and N2 (Lubkowski et al., 1998). A second vector, pTFT74-H-N1-MCS, was generated which contains between the unique NcoI and HindIII sites a DNA sequence coding for Met-Ala, a 6×His purification tag and amino acids 2–82 of g3p of phage fd fused to a multiple cloning site and three stop codons for all 3 reading frames (FIG. 2, complete vector sequence given in appendix). Compared to the published sequence, a G to T nucleotide exchange at position 57 has been found in vector pTFT74. Into vector pTFT74-N1-MCS-H, DNA fragments generated by PCR or made as an oligonucleotide cassette coding for the amino acid sequences given below and in the legend to FIG. 3 have been cloned either between the unique BsiWI and HindIII sites or between the unique XbaI and EcoRI sites. Vector pTFT74-H-N1-MCS will be used for high throughput cloning of PCR amplified ESTs similar to the procedure described by Hua et al. (1998), but introducing appropriate restriction sites at 5' and 3' end during PCR.

This way, for oligo dT primed, directionally cloned cDNAs, only 4 primers are needed for the amplification of the insert of each cDNA cloning vector (3 forward primers for amplification of EST inserts in three-open reading frames and one reverse primer corresponding to the downstream sequence of the cDNA cloning vector). 8 primers are needed for each cDNA cloning vector for the generation of 6 PCR products covering all 6 possible reading frames of the insert.

Expression, Purification and Refolding of Fusion Proteins

Expression, purification and refolding has been done as described (C. Krebber, 1996; Krebber et al., 1997). Briefly, BL21(DE3)pLysS cells (Studier et al., 1990) were transformed with the respective pTFT74 vector (see below) and grown to an $OD_{550}$ of 0.9–1.2. Induction of N1 fusion protein expression was for 3 h with 1 mM IPTG at 37° C. N1 fusion proteins were isolated by Ni-NTA chromatography from solubilised inclusion bodies and refolded. Protein concentration during refolding was usually <1 mg/ml. The following constructs have been used:

N1-hag: N1 (amino acids 1–82 of mature g3p of phage fd containing an additional methionine residue at the N-terminus) fused to the amino acid sequence PYD-VPDYASLRSHHHHHH (SEQ ID NO:1) which includes the epitope DVPDYAS (SEQ ID NO:2) from hemagglutinin recognised by antibody 17/9 (Schulze-Gahmen et al., 1993; Krebber et al., 1995). Obtainable by cloning of an oligonucleotide cassette (made from the following 2 oligonucleotides: 5'- GTACGACGT-TCCAGACTACGCTTCCCTGCGTT CCCATCACCATCACCATCACTA-3' (SEQ ID NO:3) a n d 5'-AGCTTAGTGATGGTGATGGTGATGGGAACGC AGGGAAGCGTAGTCTGGAACGTC-3' (SEQ ID NO:4) between the BsiWI and HindIII sites of vector pTFT74-N1-MCS-H.

N1-MacI: N1 (amino acids 1–82 of mature g3p of phage fd containing an additional methionine residue at the N-terminus) fused to the amino acid sequence PYGGGSGGGSGSDIAFLIDGSGSIIPHDFRRMKEF VSTVMEQLKKSKTLFSLMQYSEEFRIHFTFKEFQ NNPNPRSLVKPITQLLGRTHTATGIRKVVRELFNI TNGARKNAFKILVVITDGEKFGDPLGYEDVIPEA DREGVIRYVIGVGDAFRSEKSRQELNTIASKPPR DHVFQVNNFEALKTIQNQLREKIFAIEGTQTGSSS SFEHEMSQE(SEQ ID NO:5) (which contains amino acids 149–353 of human CR-3 alpha chain (SWISS-PROT entry P11215)) and a C-terminal sequence containing a 6×His tag. Obtainable by PCR using cDNA of HL-60 cells as a template and oligonucleotides CR-3for (5'-GTACGTACGGGGGCGGCTCTGGTGGTGGTT CTGGTAGTGACATTGCCTTCTTGATTGATGGC-3') (SEQ ID NO:6) and CR-3rev (5'-GTAAAGCTTAGTGATGGTGATGGTGATGTCT ACCTTCGATTTCCTGAGACATCTCATGCTCA AAGGAGC-3') (SEQ ID NO:7) digest of the PCR product with restriction enzymes BsiWI and HindIII, and cloning of the fragment between the BsiWI and HindIII sites of vector pTFT74-N1-MCS-H generating vector pTFT74-N1-MacI-H.

N1 (Krebber et al., 1997)

For the N1 fusions shown in FIG. 3, DNA fragments have been amplified by PCR from cDNA clones or from genomic DNA and cloned between the XbaI and EcoRI sites of vector pTFT74-N1-MCS-H.

For screening of N1-MacI binders, a purified fragment (MacI) of human CR-3 alpha chain (SWISS-PROT entry P11215) was used which contains amino acids 149–353 of human CR-3 alpha fused to a C-terminal sequence containing a 6×His tag. Obtainable by PCR from clone pTFT74-N1-MacI-H. An ATG codon was added to the 5' end of the gene during cloning. Expression and purification was performed using standard methods (The QIAexpressionist™ $3^{rd}$ edition: A handbook for high-level expression and purification of 6×His-tagged proteins (July 1998). QIAGEN GmbH, Hilden, Germany).

Panning of the HuCAL scFv Phage Library Against N1-MacI and N1

Panning against N1-MacI and N1 and characterisation of selected scFvs was performed using standard procedures (Kay et al., 1996) and the HuCAL scFv library (WO 97/08320). N1-MacI and N1 were coated for 12 h at 4° C. at a concentration of 10 μg/ml in PBS to Nunc Maxisorb microtiter plates (# 442404). In case of N1-MacI, phages were mixed 1:1 before panning with either PBS containing 5% skim milk powder and 0.1% Tween 20 (panning NMa) or PBS containing 5% skim milk powder, 0.1% Tween 20 and 0.5 mg/ml N1-hag (panning NMb). In case of N1, phages were mixed 1:1 before panning with either PBS containing 5% skim milk powder and 0.1% Tween 20 (panning Na) or PBS containing 5% skim milk powder, 0.1% Tween 20 and 0.5 mg/ml N1 (panning Nb). Phages were incubated in these buffers for 2 h at room temperature before they were applied to the ELISA well coated with antigen. After 3 rounds of panning, 92 clones from each panning were analysed in ELISA. In pannings Na and Nb, no binders against N1 were obtained while in pannings NMa and NMb several binders against N1-MacI were selected. These binders were also tested for binding to MacI. Clones which showed a signal of at least 3× above background in ELISA were considered positive.

1. NMa

Positives against N1-MacI 77

Positives against MacI: 37

2. NMb

Positives against-N1-MacI: 85

Positives against MacI: 80

All MacI binders also recognise N1-MacI. The relatively small amounts of N1-hag used for blocking lead to a 100% increase of the number of MacI binders. There are, however, additional N-terminal linker residues in N1-MacI, so complete blocking of non MacI binders using N1-hag is not possible. For some binders a specificity ELISA was performed showing that the selected scFvs bind strongly and specifically to MacI (FIG. 4).

Example 2

Construction and Properties of Expression Vector pBAD-N1-MCS-H

The vector pBAD-N1-MSC-H is based on the expression vector pBAD/Myc-His A (Invitrogen Corporation, Carlsbad, Calif., USA), and allows the expression of proteins under the control of the tightly regulated araBAD promotor. The vector pBAD-N1-MSC-H was constructed by insertion of an expression cassette (311 bp, Nco I/Hind III fragment) comprising a coding region encoding the N1 domain followed by a multiple cloning site (MCS) and a coding region encoding a His×6-tag into pBAD/Myc-His A digested with Nco I/Hind III (4046 bp). The vector map and sequence of pBAD-N1-MCS-H are shown in FIG. 5. The advantage of this vector compared to the pTFT vectors (see Examples 1 and 2) is a tighter control of fusion protein expression which allows the cloning of potentially toxic constructs. Furthermore, no additional cloning step for the transfer from a cloning strain into an expression strain is necessary. A disadvantage is that expression yields are sometimes lower compared to pTFT vectors.

Example 3

Expression of Fusion Proteins Comprising the N1 Domain of the geneIII Protein

Cloning of Expression Vectors

The vector used for expression of N1 fusion proteins is the vector pTFT74-N1-MCS-H (FIG. 1, complete vector sequence given in appendix) as described in Example 1. Into vector pTFT74-N1-MCS-H, DNA fragments generated by PCR or made as an oligonucleotide cassette coding for (poly)peptides and proteins given in brackets below have been cloned either between the unique BsiWI and HindIII sites or between the unique XbaI and EcoRI sites generating vectors pTFT74-N1-hag (see Example 1), pTFT74-N1-MacI (see Example 1), pTFT74-N1-U1fl (N1 fused to full-length UL84 of hCMV), pTFT74-N1-U2 (N1 fused to a polypeptide containing amino acids 68–586 of UL84 of hCMV), pTFT74-N1-U4 (N1 fused to a polypeptide containing amino acids 300–586 of UL84 of hCMV), pTFT74-N1-I1fl (N1 fused to mature full-length human ICAM-1), pTFT74-N1-I3 (N1 fused to a polypeptide containing amino acids 401–480 of human ICAM-1), pTFT74-N1-I4 (N1 fused to a polypeptide containing amino acids 151–532 of human ICAM-1), pTFT74-N1-B1 (N1 fused to a polypeptide containing amino acids 1–198 of a mature human MHC classII beta chain), pTFT74-N1-A14 (N1 fused to a polypeptide containing amino acids 1–192 of a mature human MHC classII alpha chain) and pTFT74-N1-Np50 (N1 fused to a polypeptide containing amino acids 2–366 of human NF-kB p50). All constructs contain a C-terminal hexa-histidine tag for affinity purification.

High-level Expression of N1-fusion Proteins

Domain N1 of g3p of filamentous bacteriophage M13 can be over-expressed in *E. coli*, purified from inclusion bodies and refolded into active protein (Krebber et al., 1997). Different polypeptides were fused C-terminally to N1 and expressed in *E. coli* leading to high-level production and inclusion body formation (FIG. 6). In case of N1-MacI, no further purification could be achieved by N1-NTA chromatography as the inclusion bodies contained already almost exclusively N1-MacI (FIG. 6). Surprisingly, all N1 fusion proteins (10/10) were soluble after refolding at concentrations of ~0.3–1.0 mg/ml using the same refolding conditions and the purity was at least 90% (FIG. 7). Protein yields were as high as 100 mg/l of expression culture in case of N1-MacI and were usually in the range between 1 mg and 10 mg/l of expression culture.

REFERENCES

Aaronson, J. S., Eckman, B., Blevins, R. A., Borkowski, J. A., Myerson, J., Imran, S., and Elliston, K. O. (1996) Toward the development of a gene index to the human genome: an assessment of the nature of high-throughput EST sequence data. Genome Res., 6, 829–845.

Adams, M. D., Kerlavage, A. R., Fleischmann, R. D., Fuldner, R. A., Bult, C. J., Lee, N. H., Kirkness, E. F., Weinstock, K.G., Gocayne, J. D., and White, O. (1995) Initial assessment of human gene diversity and expression patterns based upon 83 million nucleotides of cDNA sequence. Nature, 377, 3–174.

Ausubel, F. M., Brent, R., Kingston, R. E., Moore, D. D., Sedman, J. G., Smith, J. A., & Struhl, K. eds. (1995).

Current Protocols in Molecular Biology. New York: John Wiley and Sons.

Betton, J. & Hofnung, M. (1996). Folding of a mutant maltose-binding protein of *Escherichia coli* which forms inclusion bodies. J.Biol.Chem., 271, 8046–8052.

Bird, R. E., Hardman, K. D., Jacobson, J. W., Johnson, S., Kaufman, B. M., Lee S. M., Lee T., Pope S. H., Riordan G. S., & Whitlow M. (1988). Single-chain antigen-binding proteins [published erratum appears in (1989). Science 244, 409]. Science 242, 423–6.

Blake, M. S., Johnston, K. H., Russel-Jones, G. J. & Gotschlich, E. C. (1984). A rapid, sensitive method for detection of alkaline phosphatase-conjugated anti-antibody on Western blots. Anal. Biochem. 136, 175–179.

Boder, E. T. & Wittrup, K. D. (1997). Yeast surface display for screening combinatorial polypeptide libraries. Nat Biotechnol, 15, 553–557.

Borman, S. (1999) Reducing time to drug discovery. Recent advances in solid-phase synthesis, informatics, and high-throughput screening suggest combinatorial chemistry is coming of age. C&EN, 77, 33–48.

Bouck, J., Yu, W., Gibbs, R., and Worley, K. (1999) Comparison of gene indexing databases. Trends Genet., 15, 159–162.

Brinkmann, U., Reiter, Y., Jung, S., Lee, B. & Pastan, I (1993). A recombinant immunotoxin containing a disulfide-stabilized Fv fragment. Proc. Natl. Acad. Sci. U.S.A. 90, 7538–7542.

Chatterjee, D. K., Fujimura, R. K., Campbell, J. H., & Gerard, G. F. (1991). Cloning and overexpression of the gene encoding bacteriophage T5 DNA polymerase. Gene, 97, 13–19.

Cho, B. K., Kieke, M. C., Boder, E. T., Wittrup, K. D., & Kranz, D. M. (1998). A yeast surface display system for the discovery of ligands that trigger cell activation. J Immunol Methods, 220, 179–188.

Coburn, G. A. & Mackie, G. A. (1996). Overexpression, purification, and properties of *Escherichia coli* ribonuclease II. J.Biol.Chem., 271, 1048–1053.

Collins, F. and Galas, D. (1993) A new five-year plan for the U.S. Human Genome Project [see comments]. Science, 262, 43–46.

Crissman, J. W. & Smith, G. P. (1984). Gene-III protein of filamentous phages: evidence for a carboxy-terminal domain with a role in morphogenesis. Virology 132, 445–455.

Cull, M. G., Miller, J. F., & Schatz, P. J. (1992). Screening for receptor ligands using large libraries of peptides linked to the C terminus of the lac repressor. Proc.Natl.Acad.Sci.U.S.A, 89, 1865–1869.

Daugherty, P. S., Chen, G., Olsen, M. J., Iverson, B. L., & Georgiou, G. (1998). Antibody affinity maturation using bacterial surface display. Protein Eng, 11, 825–832.

Dekker, N., Merck, K., Tommassen, J., & Verheij, H. M. (1995). In vitro folding of *Escherichia coli* outer-membrane phospholipase A. Eur.J.Biochem, 232, 214–219.

Derman, A. I. & Beckwith, J. (1995). *Escherichia coli* alkaline phosphatase localized to the cytoplasm slowly acquires enzymatic activity in cells whose growth has been suspended: a caution for gene fusion studies. J.Bacteriol., 177, 3764–3770.

Dunn, I. S. 1996. Phage display of proteins. Curr. Opin. Biotechnol. 7:547–553.

Eckman, B. A., Aaronson, J. S., Borkowski, J. A., Bailey, W. J., Elliston, K. O., Williamson, A. R., and Blevins, R. A. (1998) The Merck Gene Index browser: an extensible data integration system for gene finding, gene characterization and EST data mining. Bioinformatics.; 14, 2–13.

Eisele, F., Owen, D. J., & Waldmann, H. (1999) Peptide conjugates as tools for the study of biological signal transduction. Bioorg. Med. Chem., 7, 193–224.

Ernst, W., Grabherr, R., Wegner, D., Borth, N., Grassauer, A., & Katinger, H: (1998). Baculovirus surface display: construction and screening of a eukaryotic epitope library. Nucleic Acids Res, 26, 1718–1723.

Ernst, W., Grabherr, R., Wegner, D., Borth, N., Grassauer, A., & Katinger, H. (1998). Baculovirus surface display: construction and screening of a eukaryotic epitope library. Nucleic Acids Res; 26, 1718–1723.

Francisco, J. A. & Georgiou, G. (1994). The expression of recombinant proteins on the external surface of *Escherichia coli*. Biotechnological applications. Ann.N.Y.Acad.Sci., 745, 372–382.

Freund, C., Ross, A., Guth, B., Plückthun, A. & Holak, T. A. (1993). Characterization of the linker peptide of the single-chain Fv fragment of an antibody by NMR spectroscopy. FEBS Lett. 320, 97–100.

Gates, C. M., Stemmer, W. P., Kaptein, R., & Schatz, P. J. (1996). Affinity selective isolation of ligands from peptide libraries through display on a lac repressor "headpiece dimer". J.Mol.Biol., 255, 373–386.

Ge, L., Knappik, A., Pack, P., Freund, C. & Plückthun, A. (1995). Expressing antibodies in *Escherichia coli*. Antibody Engineering. A Practical Approach (Ed. C. A. K. Borrebaeck). IRL Press, Oxford, pp. 229–266.

Georgiou, G., Poetschke, H. L., Stathopoulos, C., & Francisco, J. A. (1993). Practical applications of engineering gram-negative bacterial cell surfaces. Trends Biotechnol., 11, 6–10.

Glockshuber, R., Malia, M., Pfitzinger, I. & Plückthun, A. (1992). A comparison of strategies to stabilize immunoglobulin Fv-fragments. Biochemistry 29, 1362–1366.

Hanes, J. & Pluckthun, A. (1997). In vitro selection and evolution of functional proteins by using ribosome display. Proc.Natl.Acad.Sci.U.S.A, 94, 4937–4942.

Hanes, J., Jermutus, L., Schaffitzel, C., & Pluckthun, A. (1999). Comparison of *Escherichia coli* and rabbit reticulocyte ribosome display systems. FEBS Lett., 450, 105–110.

Hanes, J., Jermutus, L., Weber-Bornhauser, S., Bosshard, H. R., & Pluckthun, A. (1998). Ribosome display efficiently selects and evolves high-affinity antibodies in vitro from immune libraries. Proc.Natl.Acad.Sci.U.S.A, 95, 14130–14135.

Hiatt, A. & Ma, J. K. (1993). Characterization and applications of antibodies produced in plants. Int. Rev. Immunol. 10, 139–152.

Hiatt, A. (1990). Antibodies produced in plants. Nature 344, 469–470.

Hochuli, E., Bannwarth, W., Döbeli, H., Gentz, R. & Stüber, D. (1988). Genetic approach to facilitate purification of recombinant proteins with a novel metal chelate adsorbent. Bio/Technology 6, 1321–1325.

Holliger, P. & Riechmann, L. (1997). A conserved infection pathway for filamentous bacteriophages is suggested by the structure of the membrane penetration domain of the minor coat protein g3p from phage fd. Structure 5, 265–275.

Hoog, J. O., Bahr-Lindstrom, H., Josephson, S., Wallace, B. J., Kushner, S. R., Jornval, H., & Holmgren, A. (1984). Nucleotide sequence of the thioredoxin gene from *Escherichia coli*. Biosci.Rep., 4, 917–923.

Hopp, T. P., Prickett, K. S., Price, V. L., Libby, R. T., March, C. J., Cerretti, D. P., Urdal, D. L. & Conlon, P. J. (1988).

A short polypeptide marker sequence useful for recombinant protein identification and purification. Bio/Technology 6, 1204–1210.

Horwitz, A. H., Chang, C. P., Better, M., Hellstrom, K. E. & Robinson, R. R. (1988). Secretion of functional antibody and Fab fragment from yeast cells. Proc. Natl. Acad. Sci. U.S.A. 85, 8678–8682.

Hua, S., Luo, Y., Qiu, M., Chan, E., Zhou, H. & Zhu, L. (1998). Construction of a modular yeast two-hybrid cDNA library from human EST clones for the human genome protein linkage map. Gene 215, 143–152.

Huston, J. S., Levinson, D., Mudgett-Hunter, M., Tai, M. S., Novotny, J., Margolies, M. N., Ridge, R. J., Bruccoleri, R. E., Haber, E. & Crea, R. (1988). Protein engineering of antibody binding sites. recovery of specific activity in an anti-digoxin single-chain Fv analogue produced in *Escherichia coli*. Proc. Natl. Acad. Sci. U.S.A. 85, 5879–83.

Kay, B. K., Winter, J. & McCafferty, J., eds. (1996). Phage display of peptides and proteins: a laboratory manual. Academic Press, Inc., San Diego.

Kieke, M. C., Cho, B. K., Boder, E. T., Kranz, D. M., & Wittrup, K. D. (1997). Isolation of anti-T cell receptor scFv mutants by yeast surface display. Protein Eng, 10, 1303–1310.

Kieke, M. C., Shusta, E. V., Boder, E. T., Teyton, L., Wittrup, K. D., & Kranz, D. M. (1999). Selection of functional T cell receptor mutants from a yeast surface-display library. Proc Natl Acad Sci USA, 96, 5651–5656.

Knappik, A., Ge, L., Honegger, A., Pack, P., Fischer, M., Wellnhofer, G., Hoess, A., Wölle, J., Plückthun, A. & Virnekäs, B. (2000). Fully Synthetic Human Combinatorial Antibody Libraries (HuCAL) Based on Modular Consensus Frameworks and CDRs Randomized with Trinucleotides. J. Mol. Biol. 296, 57–86.

Knappik, A. & Plückthun, A. (1994). An improved affinity tag based on the FLAG peptide for detection and purification of recombinant antibody fragments. BioTechniques 17, 754–761.

Knappik, A., & Plückthun, A. (1994). An Improved Affinity Tag Based on the FLAG Peptide for the Detection and Purification of Recombinant Antibody Fragments. Bio Techniques 17, 754–761

Knappik, A., Krebber, C. & Plückthun, A. (1993). The effect of folding catalysts on the in vivo folding of different antibody fragments expressed in *Escherichia coli*. Bio/Technology 11, 77–83.

Krebber, C. (1996). Selektiv infektiöse Phagen: In vivo Selektion auf Interaktionen zwischen Protein und Ligand. Dissertation at the University of Zürich.

Krebber, C., Spada, S., Desplancq, D. & Plückthun, A. (1995). Co-selection of cognate antibody-antigen pairs by selectively-infective phages. FEBS Lett. 377, 227–231.

Krebber, C., Spada, S., Desplancq, D., Krebber, A., Ge, L. & Plückthun, A. (1997). Selectively-infective phage (SIP): A mechanistic dissection of a novel in vivo selection for protein-ligand interactions. J. Mol. Biol. 268, 607–618.

Kuhelj, R., Dolinar, M., Pungercar, J., & Turk, V. (1995). The preparation of catalytically active human cathepsin B from its precursor expressed in *Escherichia coli* in the form of inclusion bodies. Eur.J.Biochem, 229, 533–539.

Lebl, M. (1999) Parallel personal comments on "classical" papers in combinatorial chemistry. Journal of Combinatorial Chemistry, 1, 3–24.

Lilie, H., Schwarz, E., & Rudolph, R. (1998). Advances in refolding of proteins produced in *E. coli*. Curr.Opin.Biotechnol., 9, 497–501.

Lindner, P., Guth, B., Wülfing, C., Krebber, C., Steipe, B., Müller, F. & Plückthun, A. (1992). Purification of native proteins from the cytoplasm and periplasm of *Escherichia coli* using IMAC and histidine tails: a comparison of proteins and protocols. Methods: A Companion to Methods Enzymol. 4, 41–56.

Lubkowski, J., Hennecke, F., Plückthun, A. & Wlodawer, A. (1998). The structural basis of phage display elucidated by the crystal structure of the N-terminal domains of g3p. Nature Struct. Biol. 5, 140–147.

McGregor, D. 1996. Selection of proteins and peptides from libraries displayed on filamentous bacteriophage. Mol. Biotechnol. 6:155–162.

Model, P. & Russel, M. (1988). Filamentous bacteriophage. p 375–456. In R. Calendar (ed.), The bacteriophages, vol. 2, Plenum, New York, N.Y.

Nemoto, N., Miyamoto-Sato, E., Husimi, Y., & Yanagawa, H. (1997). In vitro virus: bonding of mRNA bearing puromycin at the 3'-terminal end to the C-terminal end of its encoded protein on the ribosome in vitro. FEBS Lett., 414, 405–408.

Nyyssönen, E., Penttila, M., Harkki, A., Saloheimo, A., Knowles, J. K. & Keranen, S. (1993). Efficient production of antibody fragments by the filamentous fungus *Trichoderma reesei*. Bio/Technology 11, 591–595.

Persic, L., Horn, I. R., Rybak, S., Cattaneo, A., Hoogenboom, H. R., and Bradbury, A. (1999) Single-chain variable fragments selected on the 57–76 p21Ras neutralising epitope from phage antibody libraries recognise the parental protein. FEBS Lett., 443, 112–116.

Pinilla, C., Martin, R., Gran, B., Appel, J. R., Boggiano, C., Wilson, D. B., & Houghten, R. A. (1999) Exploring immunological specificity using synthetic peptide combinatorial libraries. Curr. Opin. Immunol., 11, 193–202.

Potter, K. N., Li, Y. & Capra, J. D. (1993). Antibody production in the baculovirus expression system. Int. Rev. Immunol. 10, 103–112.

Ridder, R., Schmitz, R., Legay, F. & Gram, H. (1995). Generation of rabbit monoclonal antibody fragments from a combinatorial phage display library and their production in the yeast Pichia pastoris. Bio/Technology 13, 255–260.

Riechmann, L. & Holliger, P. (1997). The C-terminal domain of TolA is the coreceptor for filamentous phage infection of *E. coli*. Cell 90, 351–360.

Rinas, U. & Bailey, J. E. (1993). Overexpression of bacterial hemoglobin causes incorporation of pre-beta-lactamase into cytoplasmic inclusion bodies. Appl.Environ.Microbiol., 59, 561–566.

Rudolph, R. (1996). Successful Protein Folding on an Industrial Scale. Protein Engineering. Principles and Practice (Eds. Cleland, J. L., Craik, C. S.). Wiley-Liss, New York, pp. 283–298.

Rudolph, R. & Lilie, H. (1996). In vitro folding of inclusion body proteins. FASEB J., 10, 49–56.

Rudolph, R., Böhm, G., Lilie, H. & Jaenicke, R. (1997). Folding Proteins. Protein Folding. A Practical Approach, edn 2 (Ed. Creighton, T. E.). IRL Press, Oxford, pp. 57–99.

Russell, S. J., Hawkins, R. E., & Winter, G. (1993). Retroviral vectors displaying functional antibody fragments. Nucleic Acids Res, 21, 1081–1085.

Sambrook, J., Fritsch, E. F. and Maniatis, T. (1989) Molecular Cloning: A laboratory manual, Cold Spring Harbor Laboratory Press, Cold Spring Harbor, USA.

Schatz, P. J. (1993). Use of peptide libraries to map the substrate specificity of a peptide-modifying enzyme: a 13 residue consensus peptide specifies biotinylation in *Escherichia coli*. Biotechnology (N.Y.), 11, 1138–1143.

Schatz, P. J., Cull, M. G., Martin, E. L., & Gates, C. M. (1996). Screening of peptide libraries linked to lac repressor. Methods Enzymol., 267, 171–191.

Schmidt, T. G. & Skerra, A. (1993). The random peptide library-assisted engineering of a C-terminal affinity peptide, useful for the detection and purification of a functional Ig Fv fragment. Protein Eng, 6, 109–122.

Schmidt, T. G. & Skerra, A. (1994). One-step affinity purification of bacterially produced proteins by means of the "Strep tag" and immobilized recombinant core streptavidin. J.Chromatogr.A, 676, 337–345.

Schmidt, T. G., Koepke, J., Frank, R., & Skerra, A. (1996). Molecular interaction between the Strep-tag affinity peptide and its cognate target, streptavidin. J.Mol.Biol., 255, 753–766.

Schulze-Gahmen, U., Rini, J. M. & Wilson, I. A. (1993). Detailed analysis of the free and bound conformations of an antibody: X-ray structures of Fab 17/9 and three different Fab-peptide complexes. J. Mol. Biol. 234, 1098–1118.

Skerra, A. & Plückthun(1988). Assembly of a functional immunoglobulin Fv fragment in *Escherichia coli*. Science 240, 1038–1041.

Stengele, I., Bross, P., Garcés, X., Giray, J. & Rasched, I. (1990). Dissection of functional domains in phage fd adsorption protein. J. Mol. Biol. 212, 143–149.

Studier, F. W., Rosenberg, A. H., Dunn, J. J. & Dubendorff, J. W. (1990). Use of T7 RNA polymerase to direct the expression of cloned genes. Meth. Enzymol. 185, 60–89.

Sykes, K. F. and Johnston, S. A. (1999) Linear expression elements: a rapid, in vivo, method to screen for gene functions. Nat.Biotechnol:, 17, 355–359.

Trill, J. J., Shatzman, A. R. & Ganguly, S. (1995). Production of monoclonal antibodies in COS and CHO cells. Curr. Opin. Biotechnol. 6, 553–560.

Vandenbroeck, K., Martens, E., D'Andrea, S., & Billiau, A. (1993). Refolding and single-step purification of porcine interferon-gamma from *Escherichia coli* inclusion bodies. Conditions for reconstitution of dimeric IFN-gamma. Eur.J.Biochem, 215, 481–486.

Vaughan, T. J., Williams, A. J., Pritchard, K., Osborn, J. K., Pope, A. R., Earnshaw, J. C., McCafferty, J., Hodits, R. A., Wilton, J. and Johnson, K. S. 1996. Human antibodies with sub-nanomolar affinities isolated from a large non-immunized phage display library. Nature Biotechnology 14:309–314.

Ward, V. K., Kreissig, S. B., Hammock, B. D. & Choudary, P. V. (1995). Generation of an expression library in the baculovirus expression vector system. J. Virol. Methods 53, 263–272.

Whitelam, G. C., Cockburn, W. & Owen, M. R. (1994). Antibody production in transgenic plants. Biochem. Soc. Trans. 22, 940–944.

Woodbury, C. P, & Venton, D. L. (1999) Methods of screening combinatorial libraries using immobilized or restrained receptors. Journal of Chromatography B, 725, 113–137.

Wu, X. C., Ng, S. C., Near, R. I. & Wong, S. L. (1993). Efficient production of a functional single-chain anti-digoxin antibody via an engineered *Bacillus subtilis* expression-secretion system. Bio/Technology 11, 71–76.

---

What is claimed is:

1. A method for generating a specific binding partner to a (poly)peptide which is encoded by a nucleic acid sequence comprised in a genomic DNA fragment or an expressed sequence tag (EST) comprising:
 a) expressing a nucleic acid molecule encoding a fusion protein in a host cell under conditions that allow the formation of inclusion bodies comprising said fusion protein, wherein said fusion protein comprises
  aa) a (poly)peptide or protein fusion partner which is deposited in inclusion bodies when expressed in said host cell under said conditions, and
  ab) said (poly)peptide;
 b) isolating said inclusion bodies; and
 c) generating a specific binding partner that binds specifically to said (poly)peptide by screening or selecting against (i) said isolated inclusion bodies or (ii) said fusion protein obtained from said inclusion bodies, wherein said fusion partner is a secreted protein, and wherein said nucleic acid does not comprise a nucleic acid sequence encoding a signal sequence for the transport of the fusion protein to the periplasm.

2. The method of claim 1, wherein said fusion protein comprises said fusion partner as N-terminal portion and said (poly)peptide as C-terminal portion.

3. The method of claim 1, wherein said fusion protein further comprises a (poly)peptide linker linking said fusion partner and said (poly)peptide.

4. The method of claim 3, wherein said linker comprises a cleavage signal.

5. The method of claim 1, wherein said genomic DNA fragment or said EST is obtained from a prokaryotic organism or from a virus.

6. The method of claim 5, wherein said prokaryotic organism or virus is a pathogen.

7. The method of claim 1, wherein said genomic DNA fragment or said EST is obtained from a eukaryotic organism.

8. The method of claim 7, wherein said genomic DNA fragment or EST is obtained from a non-mammalian species.

9. The method of claim 7, wherein said genomic DNA fragment or EST is obtained from a mammalian species.

10. The method of claim 9, wherein said mammalian species is human.

11. The method of claim 1, wherein said nucleic acid is expressed under conditions allowing over-expression of said fusion protein.

12. The method of claim 1, wherein said host cell is a eukaryotic cell.

13. The method of claim 12, wherein said eukaryotic cell is a yeast or insect cell.

14. The method of claim 1, wherein said host cell is a prokaryotic cell.

15. The method of claim 14, wherein said prokaryotic cell is a bacterial cell.

16. The method of claim 15, wherein said bacterial cell is an E. coli cell.

17. The method of claim 15, wherein said fusion protein is expressed in the cytosol.

18. The method of claim 17, wherein said fusion partner contains at least one disulfide bond.

19. The method of claim 1, wherein said fusion partner is an endogenous (poly)peptide/protein of said host cell.

20. A method for generating a specific binding partner to a (poly)peptide which is encoded by a nucleic acid sequence comprised in a genomic DNA fragment or an expressed sequence tag (EST) comprising:
 a) expressing a nucleic acid molecule encoding a fusion protein in a host cell under conditions that allow the formation of inclusion bodies comprising said fusion protein, wherein said fusion protein comprises
  aa) a (poly)peptide or protein fusion partner which is deposited in inclusion bodies when expressed in said host cell under said conditions, and
  ab) said (poly)peptide;
 b) isolating said inclusion bodies; and
 c) generating a specific binding partner that binds specifically to said (poly)peptide by screening or selecting against (i) said isolated inclusion bodies or (ii) said fusion protein obtained from said inclusion bodies, wherein said fusion partner is selected from the group consisting of E. coli maltose-binding protein, E. coli RNAse II, E. coli alkaline phosphatase, E. coli phospholipase A, E. coli β-lactamase, E. coli thioredoxin, human procathepsin B, porcine interferon, and T5 DNA polymerase.

21. A method for generating a specific binding partner to a (poly)peptide which is encoded by a nucleic acid sequence comprised in a genomic DNA fragment or an expressed sequence tag (EST) comprising:
 a) expressing a nucleic acid molecule encoding a fusion protein in a host cell under conditions that allow the formation of inclusion bodies comprising said fusion protein, wherein said fusion protein comprises aa) a (poly)peptide or protein fusion partner which is deposited in inclusion bodies when expressed in said host cell under said conditions, and ab) said (poly)peptide;

b) isolating said inclusion bodies; and c) generating a specific binding partner that binds specifically to said (poly)peptide by screening or selecting against (i) said isolated inclusion bodies or (ii) said fusion protein obtained from said inclusion bodies, wherein said fusion partner is a (poly)peptide or protein foreign to said host cell, and wherein said host cell is *E. coli* and said fusion partner comprises the first N-terminal domain of the geneIII protein of a filamentous phage.

22. The method of claim 21, wherein said fusion partner consists of amino acids 1 to 82 of the geneIII protein.

23. The method of claim 1, wherein step b) further comprises the step of (i) solubilising said fusion protein under suitable conditions.

24. The method of claim 23, wherein step b) further comprises the step of (ii) refolding said fusion protein under suitable conditions.

25. The method of claim 23, wherein said fusion protein further comprises a (poly)peptide linker linking said fusion partner and said (poly)peptide, wherein said linker comprises a cleavage signal, and wherein step b) further comprises the steps of (iii) cleaving said fusion protein between said fusion partner and said (poly)peptide, and (iv) isolating said (poly)peptide in free form.

26. The method of claim 24, wherein said fusion protein further comprises a (poly)peptide linker linking said fusion partner and said (poly)peptide, wherein said linker comprises a cleavage signal, and wherein step b) further comprises the steps of (iii) cleaving said fusion protein between said fusion partner and said (poly)peptide, and (iv) isolating said (poly)peptide in free form.

27. The method of any one of claims 23 to 25, and 26 further comprising the step of purifying said fusion protein or said (poly)peptide in free form.

28. The method of claim 1, wherein said specific binding partner is an immunoglobulin or a fragment thereof.

29. The method of claim 28, wherein said immunoglobulin is generated by (i) immunisation of an animal with said inclusion bodies, said fusion protein or said (poly)peptide, and (ii) by selecting an immunoglobulin produced by said animal which specifically binds to said inclusion bodies, said fusion protein or said (poly)peptide.

30. The method of claim 28 wherein said immunoglobulin or fragment thereof is generated by selecting a member of a recombinant library of immunoglobulins or fragments thereof which specifically binds to said inclusion bodies, said fusion protein or said (poly)peptide.

31. The method of claim 30, wherein said library is displayed on the surface of a replicable genetic package.

32. The method of claim 31 wherein said replicable genetic package is a filamentous phage.

* * * * *

SEQUENCE LISTING

<160> NUMBER OF SEQ ID NOS: 10

<210> SEQ ID NO 1
<211> LENGTH: 18
<212> TYPE: PRT
<213> ORGANISM: artificial sequence
<220> FEATURE:
<221> NAME/KEY: PEPTIDE
<222> LOCATION: (1)..(18)
<223> OTHER INFORMATION: synthetic expression construct

<400> SEQUENCE: 1

Pro Tyr Asp Val Pro Asp Tyr Ala Ser Leu Arg Ser His His His His
1               5                   10                  15

His His

<210> SEQ ID NO 2
<211> LENGTH: 7
<212> TYPE: PRT
<213> ORGANISM: artificial sequence
<220> FEATURE:
<221> NAME/KEY: PEPTIDE
<222> LOCATION: (1)..(7)
<223> OTHER INFORMATION: synthetic construct
      hemagglutinin epitope

<400> SEQUENCE: 2

Asp Val Pro Asp Tyr Ala Ser
1               5

<210> SEQ ID NO 3
<211> LENGTH: 54

```
<212> TYPE: DNA
<213> ORGANISM: artificial sequence
<220> FEATURE:
<221> NAME/KEY: misc_feature
<222> LOCATION: (1)..(54)
<223> OTHER INFORMATION: DNA primer for cloning of an oligonucleotide
      cassette

<400> SEQUENCE: 3
gtacgacgtt ccagactacg cttccctgcg ttcccatcac catcaccatc acta        54

<210> SEQ ID NO 4
<211> LENGTH: 54
<212> TYPE: DNA
<213> ORGANISM: artificial sequence
<220> FEATURE:
<221> NAME/KEY: misc_feature
<222> LOCATION: (1)..(54)
<223> OTHER INFORMATION: DNA primer for cloning of an oligonucleotide
      cassette

<400> SEQUENCE: 4
agcttagtga tggtgatggt gatgggaacg cagggaagcg tagtctggaa cgtc        54

<210> SEQ ID NO 5
<211> LENGTH: 216
<212> TYPE: PRT
<213> ORGANISM: artificial sequence
<220> FEATURE:
<221> NAME/KEY: PEPTIDE
<222> LOCATION: (1)..(216)
<223> OTHER INFORMATION: synthetic contsruct
      contains amino acids 149-353 of human CR-3 alpha chain

<400> SEQUENCE: 5
```

Pro Tyr Gly Gly Gly Ser Gly Gly Ser Gly Ser Asp Ile Ala Phe
1               5                   10                  15

Leu Ile Asp Gly Ser Gly Ser Ile Ile Pro His Asp Phe Arg Arg Met
            20                  25                  30

Lys Glu Phe Val Ser Thr Val Met Glu Gln Leu Lys Lys Ser Lys Thr
            35                  40                  45

Leu Phe Ser Leu Met Gln Tyr Ser Glu Glu Phe Arg Ile His Phe Thr
50                  55                  60

Phe Lys Glu Phe Gln Asn Asn Pro Asn Pro Arg Ser Leu Val Lys Pro
65                  70                  75                  80

Ile Thr Gln Leu Leu Gly Arg Thr His Thr Ala Thr Gly Ile Arg Lys
            85                  90                  95

Val Val Arg Glu Leu Phe Asn Ile Thr Asn Gly Ala Arg Lys Asn Ala
            100                 105                 110

Phe Lys Ile Leu Val Val Ile Thr Asp Gly Glu Lys Phe Gly Asp Pro
            115                 120                 125

Leu Gly Tyr Glu Asp Val Ile Pro Glu Ala Asp Arg Glu Gly Val Ile
            130                 135                 140

Arg Tyr Val Ile Gly Val Gly Asp Ala Phe Arg Ser Glu Lys Ser Arg
145                 150                 155                 160

Gln Glu Leu Asn Thr Ile Ala Ser Lys Pro Pro Arg Asp His Val Phe
                165                 170                 175

Gln Val Asn Asn Phe Glu Ala Leu Lys Thr Ile Gln Asn Gln Leu Arg
            180                 185                 190

Glu Lys Ile Phe Ala Ile Glu Gly Thr Gln Thr Gly Ser Ser Ser Ser
            195                 200                 205

Phe Glu His Glu Met Ser Gln Glu
    210                 215

<210> SEQ ID NO 6
<211> LENGTH: 62
<212> TYPE: DNA
<213> ORGANISM: artificial sequence
<220> FEATURE:
<221> NAME/KEY: misc_feature
<222> LOCATION: (1)..(62)
<223> OTHER INFORMATION: synthetic construct
     DNA forward primer

<400> SEQUENCE: 6

```
gtacgtacgg gggcggctct ggtggtggtt ctggtagtga cattgccttc ttgattgatg    60
gc                                                                   62
```

<210> SEQ ID NO 7
<211> LENGTH: 69
<212> TYPE: DNA
<213> ORGANISM: artificial sequence
<220> FEATURE:
<221> NAME/KEY: misc_feature
<222> LOCATION: (1)..(69)
<223> OTHER INFORMATION: synthetic construct
     DNA reverse primer

<400> SEQUENCE: 7

```
gtaaagctta gtgatggtga tggtgatgtc taccttcgat ttcctgagac atctcatgct    60
caaaggagc                                                            69
```

<210> SEQ ID NO 8
<211> LENGTH: 2869
<212> TYPE: DNA
<213> ORGANISM: artificial sequence
<220> FEATURE:
<221> NAME/KEY: misc_feature
<222> LOCATION: (1)..(2869)
<223> OTHER INFORMATION: synthetic construct
     expression vector

<400> SEQUENCE: 8

```
acccgacacc atcgaaatta atacgactca ctatagggag accacaacgg tttccctaat    60
tgtgagcgga taacaataga ataattttg tttaacttta agaaggagat atatccatgg    120
ctgaaactgt tgaaagttgt ttagcaaaat cccatacaga aaattcattt actaacgtct    180
ggaaagacga caaaacttta gatcgttacg ctaactatga gggctgtctg tggaatgcta    240
caggcgttgt agtttgtact ggtgacgaaa ctcagtgtta cggtacatgg gttcctattg    300
ggcttgctat ccctgaaaat gagggtggtg gctctgaggg tggcggttct gagggtggcg    360
gttctccgta cggctctaga gtcgacgagc tcgatatcgg cggccgcgaa ttctctcatc    420
accatcacca tcactaagct tcagtcccgg gcagtggatc cggctgctaa caaagcccga    480
aaggaagctg agttggctgc tgccaccgct gagcaataac tagcataacc ccttggggcc    540
tctaaacggg tcttgagggg ttttttgctg aaaggaggaa ctatatccgg atcgagatcc    600
ccacgcgccc tgtagcggcg cattaagcgc ggcgggtgtg gtggttacgc gcagcgtgac    660
cgctacactt gccagcgccc tagcgcccgc tcctttcgct ttcttccctt cctttctcgc    720
cacgttcgcc ggctttcccc gtcaagctct aaatcgggc atccctttag ggttccgatt    780
tagtgcttta cggcacctcg accccaaaaa acttgattag ggtgatggtt cacgtagtgg    840
gccatcgccc tgatagacgg ttttcgccc tttgacgttg gagtccacgt tctttaatag    900
```

```
tggactcttg ttccaaactg aacaacact caaccctatc tcggtctatt cttttgattt      960
ataagggatt ttgccgattt cggcctattg gttaaaaaat gagctgattt aacaaaaatt    1020
taacgcgaat tttaacaaaa tattaacgtt tacaatttca ggtggcactt ttcggggaaa    1080
tgtgcgcgga acccctattt gtttattttt ctaaatacat tcaaatatgt atccgctcat    1140
gagacaataa ccctgataaa tgcttcaata atattgaaaa aggaagagta tgagtattca    1200
acatttccgt gtcgccctta ttccctttt tgcggcattt tgccttcctg ttttttgctca    1260
cccagaaacg ctggtgaaag taaaagatgc tgaagatcag ttgggtgcac gagtgggtta   1320
catcgaactg gatctcaaca gcggtaagat ccttgagagt tttcgccccg aagaacgttt   1380
tccaatgatg agcactttta aagttctgct atgtggcgcg gtattatccc gtattgacgc   1440
cgggcaagag caactcggtc gccgcataca ctattctcag aatgacttgg ttgagtactc   1500
accagtcaca gaaaagcatc ttacggatgg catgacagta agagaattat gcagtgctgc   1560
cataaccatg agtgataaca ctgcggccaa cttacttctg acaacgatcg gaggaccgaa   1620
ggagctaacc gcttttttgc acaacatggg ggatcatgta actcgccttg atcgttggga   1680
accggagctg aatgaagcca taccaaacga cgagcgtgac accacgatgc ctgtagcaat   1740
ggcaacaacg ttgcgcaaac tattaactgg cgaactactt actctagctt cccggcaaca   1800
attaatagac tggatggagg cggataaagt tgcaggacca cttctgcgct cggcccttcc   1860
ggctggctgg tttattgctg ataaatctgg agccggtgag cgtgggtctc gcggtatcat   1920
tgcagcactg gggccagatg gtaagccctc ccgtatcgta gttatctaca cgacggggag   1980
tcaggcaact atggatgaac gaaatagaca gatcgctgag ataggtgcct cactgattaa   2040
gcattggtaa ctgtcagacc aagtttactc atatatactt tagattgatt taaaacttca   2100
tttttaattt aaaaggatct aggtgaagat cctttttgat aatctcatga ccaaaatccc   2160
ttaacgtgag ttttcgttcc actgagcgtc agaccccgta gaaaagatca aggatcttc    2220
ttgagatcct ttttttctgc gcgtaatctg ctgcttgcaa acaaaaaaac caccgctacc   2280
agcggtggtt tgtttgccgg atcaagagct accaactctt tttccgaagg taactggctt   2340
cagcagagcg cagataccaa atactgtcct tctagtgtag ccgtagttag gccaccactt   2400
caagaactct gtagcaccgc ctacatacct cgctctgcta atcctgttac cagtggctgc   2460
tgccagtggc gataagtcgt gtcttaccgg gttggactca agacgatagt taccggataa   2520
ggcgcagcgg tcgggctgaa cggggggttc gtgcacacag cccagcttgg agcgaacgac   2580
ctacaccgaa ctgagatacc tacagcgtga gctatgagaa agcgccacgc ttcccgaagg   2640
gagaaaggcg gacaggtatc cggtaagcgg cagggtcgga acaggagagc gcacgaggga   2700
gcttccaggg ggaaacgcct ggtatcttta tagtcctgtc gggtttcgcc acctctgact   2760
tgagcgtcga ttttgtgat gctcgtcagg ggggcggagc ctatgaaaaa acgccagcaa    2820
cgcggccttt ttacggttcc tggccttttg ctggcctttt gctcacatg                2869
```

<210> SEQ ID NO 9  
<211> LENGTH: 2865  
<212> TYPE: DNA  
<213> ORGANISM: artificial sequence  
<220> FEATURE:  
<221> NAME/KEY: misc_feature  
<222> LOCATION: (1)..(2865)  
<223> OTHER INFORMATION: synthetic construct  
     expression vector

<400> SEQUENCE: 9

-continued

```
acccgacacc atcgaaatta atacgactca ctataggag accacaacgg tttccctaat      60
tgtgagcgga taacaataga aataattttg tttaacttta agaaggagat atatccatgg    120
ctcatcacca tcaccatcac gaaactgttg aaagttgttt agcaaaatcc catacagaaa    180
attcatttac taacgtctgg aaagacgaca aaactttaga tcgttacgct aactatgagg    240
gctgtctgtg gaatgctaca ggcgttgtag tttgtactgg tgacgaaact cagtgttacg    300
gtacatgggt tcctattggg cttgctatcc ctgaaaatga gggtggtggc tctgagggtg    360
gcggttctga gggtggcggt tcttctagag tcgacgagct cgatatcgaa ttcggcggcc    420
gctaactgac taagcttcag tcccgggcag tggatccggc tgctaacaaa gcccgaaagg    480
aagctgagtt ggctgctgcc accgctgagc aataactagc ataacccctt ggggcctcta    540
aacgggtctt gaggggtttt ttgctgaaag gaggaactat atccggatcg agatccccac    600
gcgccctgta gcggcgcatt aagcgcggcg ggtgtggtgg ttacgcgcag cgtgaccgct    660
acacttgcca gcgccctagc gcccgctcct ttcgctttct tcccttcctt tctcgccacg    720
ttcgccggct ttccccgtca agctctaaat cggggcatcc ctttagggtt ccgatttagt    780
gctttacggc acctcgaccc caaaaaactt gattagggtg atggttcacg tagtgggcca    840
tcgccctgat agacggtttt tcgccctttg acgttggagt ccacgttctt aatagtgga    900
ctcttgttcc aaactggaac aacactcaac cctatctcgg tctattcttt tgatttataa    960
gggattttgc cgatttcggc ctattggtta aaaaatgagc tgatttaaca aaaatttaac   1020
gcgaatttta acaaaatatt aacgtttaca atttcaggtg gcacttttcg gggaaatgtg   1080
cgcggaaccc ctatttgttt attttttctaa atacattcaa atatgtatcc gctcatgaga   1140
caataaccct gataaatgct tcaataatat tgaaaaagga agagtatgag tattcaacat   1200
ttccgtgtcg cccttattcc cttttttgcg gcattttgcc ttcctgtttt tgctcaccca   1260
gaaacgctgg tgaaagtaaa agatgctgaa gatcagttgg gtgcacgagt gggttacatc   1320
gaactggatc tcaacagcgg taagatcctt gagagttttc gccccgaaga acgttttcca   1380
atgatgagca cttttaaagt tctgctatgt ggcgcggtat tatcccgtat tgacgccggg   1440
caagagcaac tcggtcgccg catacactat tctcagaatg acttggttga gtactcacca   1500
gtcacagaaa agcatcttac ggatggcatg acagtaagag aattatgcag tgctgccata   1560
accatgagtg ataacactgc ggccaactta cttctgacaa cgatcggagg accgaaggag   1620
ctaaccgctt ttttgcacaa catgggggat catgtaactc gccttgatcg ttgggaaccg   1680
gagctgaatg aagccatacc aaacgacgag cgtgacacca cgatgcctgt agcaatggca   1740
acaacgttgc gcaaactatt aactggcgaa ctacttactc tagcttcccg gcaacaatta   1800
atagactgga tggaggcgga taaagttgca ggaccacttc tgcgctcggc ccttccggct   1860
ggctggttta ttgctgataa atctggagcc ggtgagcgtg gtctcgcgg tatcattgca   1920
gcactgggc cagatggtaa gccctcccgt atcgtagtta tctacacgac ggggagtcag   1980
gcaactatgg atgaacgaaa tagacagatc gctgagatag gtgcctcact gattaagcat   2040
tggtaactgt cagaccaagt ttactcatat atactttaga ttgatttaaa acttcatttt   2100
taatttaaaa ggatctaggt gaagatcctt tttgataatc tcatgaccaa aatcccttaa   2160
cgtgagtttt cgttccactg agcgtcagac cccgtagaaa agatcaaagg atcttcttga   2220
gatccttttt tctgcgcgt aatctgctgc ttgcaaacaa aaaaaccacc gctaccagcg   2280
gtggtttgtt tgccggatca agagctacca actctttttc cgaaggtaac tggcttcagc   2340
```

-continued

| | | | |
|---|---|---|---|
| agagcgcaga | taccaaatac | tgtccttcta | gtgtagccgt agttaggcca ccacttcaag | 2400 |
| aactctgtag | caccgcctac | atacctcgct | ctgctaatcc tgttaccagt ggctgctgcc | 2460 |
| agtggcgata | agtcgtgtct | taccggggttg | gactcaagac gatagttacc ggataaggcg | 2520 |
| cagcggtcgg | gctgaacggg | gggttcgtgc | acacagccca gcttggagcg aacgacctac | 2580 |
| accgaactga | gatacctaca | gcgtgagcta | tgagaaagcg ccacgcttcc cgaagggaga | 2640 |
| aaggcggaca | ggtatccggt | aagcggcagg | gtcggaacag gagagcgcac gagggagctt | 2700 |
| ccagggggaa | acgcctggta | tctttatagt | cctgtcgggt ttcgccacct ctgacttgag | 2760 |
| cgtcgatttt | tgtgatgctc | gtcagggggg | cggagcctat ggaaaaacgc cagcaacgcg | 2820 |
| gccttttac | ggttcctggc | cttttgctgg | ccttttgctc acatg | 2865 |

<210> SEQ ID NO 10
<211> LENGTH: 4357
<212> TYPE: DNA
<213> ORGANISM: artificial sequence
<220> FEATURE:
<221> NAME/KEY: misc_feature
<222> LOCATION: (1)..(4357)
<223> OTHER INFORMATION: synthetic construct
      expression vector

<400> SEQUENCE: 10

| | | | |
|---|---|---|---|
| aagaaaccaa | ttgtccatat | tgcatcagac | attgccgtca ctgcgtcttt tactggctct | 60 |
| tctcgctaac | caaaccggta | accccgctta | ttaaaagcat tctgtaacaa agcgggacca | 120 |
| aagccatgac | aaaaacgcgt | aacaaaagtg | tctataatca cggcagaaaa gtccacattg | 180 |
| attatttgca | cggcgtcaca | ctttgctatg | ccatagcatt tttatccata agattagcgg | 240 |
| atcctacctg | acgctttta | tcgcaactct | ctactgtttc tccatacccg ttttttggg | 300 |
| ctaacaggag | gaattaacca | tggctgaaac | tgttgaaagt tgtttagcaa atcccatac | 360 |
| agaaaattca | tttactaacg | tctggaaaga | cgacaaaact ttagatcgtt acgctaacta | 420 |
| tgagggctgt | ctgtggaatg | ctacaggcgt | tgtagtttgt actggtgacg aaactcagtg | 480 |
| ttacggtaca | tgggttccta | ttgggcttgc | tatccctgaa aatgagggtg gtggctctga | 540 |
| gggtggcggt | tctgagggtg | gcggttctag | agtcgacgag ctcgatatcg gcggccgcga | 600 |
| attctctcat | caccatcacc | atcactaagc | ttgggcccga acaaaaactc atctcagaag | 660 |
| aggatctgaa | tagcgccgtc | gaccatcatc | atcatcatca ttgagtttaa acggtctcca | 720 |
| gcttggctgt | tttggcggat | gagagaagat | tttcagcctg atacagatta aatcagaacg | 780 |
| cagaagcggt | ctgataaaac | agaatttgcc | tggcggcagt agcgcggtgg tcccacctga | 840 |
| ccccatgccg | aactcagaag | tgaaacgccg | tagcgccgat ggtagtgtgg ggtctcccca | 900 |
| tgcgagagta | gggaactgcc | aggcatcaaa | taaaacgaaa ggctcagtcg aaagactggg | 960 |
| cctttcgttt | tatctgttgt | ttgtcggtga | acgctctcct gagtaggaca atccgccgg | 1020 |
| gagcggattt | gaacgttgcg | aagcaacggc | ccggagggtg cgggcagga cgcccgccat | 1080 |
| aaactgccag | gcatcaaatt | aagcagaagg | ccatcctgac ggatggcctt tttgcgtttc | 1140 |
| tacaaactct | ttttgtttat | ttttctaaat | acattcaaat atgtatccgc tcatgagaca | 1200 |
| ataaccctga | taaatgcttc | aataatattg | aaaaggaag agtatgagta ttcaacattt | 1260 |
| ccgtgtcgcc | cttattccct | tttttgcggc | attttgcctt cctgttttg ctcacccaga | 1320 |
| aacgctggtg | aaagtaaaag | atgctgaaga | tcagttgggt gcacgagtgg gttacatcga | 1380 |
| actggatctc | aacagcggta | agatccttga | gagttttcgc cccgaagaac gttttccaat | 1440 |

-continued

```
gatgagcact tttaaagttc tgctatgtgg cgcggtatta tcccgtgttg acgccgggca    1500
agagcaactc ggtcgccgca tacactattc tcagaatgac ttggttgagt actcaccagt    1560
cacagaaaag catcttacgg atggcatgac agtaagagaa ttatgcagtg ctgccataac    1620
catgagtgat aacactgcgg ccaacttact tctgacaacg atcggaggac cgaaggagct    1680
aaccgctttt ttgcacaaca tgggggatca tgtaactcgc cttgatcgtt gggaaccgga    1740
gctgaatgaa gccataccaa cgacgagcg tgacaccacg atgcctgtag caatggcaac    1800
aacgttgcgc aaactattaa ctggcgaact acttactcta gcttcccggc aacaattaat    1860
agactggatg gaggcggata agttgcagg accacttctg cgctcggccc ttccggctgg    1920
ctggtttatt gctgataaat ctggagccgg tgagcgtggg tctcgcggta tcattgcagc    1980
actggggcca gatggtaagc cctcccgtat cgtagttatc tacacgacgg ggagtcaggc    2040
aactatggat gaacgaaata gacagatcgc tgagataggt gcctcactga ttaagcattg    2100
gtaactgtca gaccaagttt actcatatat actttagatt gatttaaaac ttcatttta    2160
atttaaaagg atctaggtga agatccttt tgataatctc atgaccaaaa tcccttaacg    2220
tgagttttcg ttccactgag cgtcagaccc cgtagaaaag atcaaaggat cttcttgaga    2280
tccttttttt ctgcgcgtaa tctgctgctt gcaaacaaaa aaaccaccgc taccagcggt    2340
ggtttgtttg ccggatcaag agctaccaac tcttttttccg aaggtaactg gcttcagcag    2400
agcgcagata ccaaatactg tccttctagt gtagccgtag ttaggccacc acttcaagaa    2460
ctctgtagca ccgcctacat acctcgctct gctaatcctg ttaccagtgg ctgctgccag    2520
tggcgataag tcgtgtctta ccgggttgga ctcaagacga tagttaccgg ataaggcgca    2580
gcggtcgggc tgaacggggg gttcgtgcac acagcccagc ttggagcgaa cgacctacac    2640
cgaactgaga tacctacagc gtgagctatg agaaagcgcc acgcttcccg aagggagaaa    2700
ggcggacagg tatccggtaa gcggcagggt cggaacagga gagcgcacga gggagcttcc    2760
agggggaaac gcctggtatc tttatagtcc tgtcgggttt cgccacctct gacttgagcg    2820
tcgatttttg tgatgctcgt caggggggcg gagcctatgg aaaaacgcca gcaacgcggc    2880
cttttttacgg ttcctggcct tttgctggcc ttttgctcac atgttctttc ctgcgttatc    2940
ccctgattct gtggataacc gtattaccgc ctttgagtga gctgataccg ctcgccgcag    3000
ccgaacgacc gagcgcagcg agtcagtgag cgaggaagcg gaagagcgcc tgatgcggta    3060
ttttctcctt acgcatctgt gcggtatttc acaccgcata tggtgcactc tcagtacaat    3120
ctgctctgat gccgcatagt taagccagta tacactccgc tatcgctacg tgactgggtc    3180
atggctgcgc cccgacaccc gccaacaccc gctgacgcgc cctgacgggc ttgtctgctc    3240
ccggcatccg cttacagaca agctgtgacc gtctccggga gctgcatgtg tcagaggttt    3300
tcaccgtcat caccgaaacg cgcgaggcag cagatcaatt cgcgcgcgaa ggcgaagcgg    3360
catgcataat gtgcctgtca aatggacgaa gcagggattc tgcaaaccct atgctactcc    3420
gtcaagccgt caattgtctg attcgttacc aattatgaca acttgacggc tacatcattc    3480
acttttctt cacaaccggc acggaactcg ctcgggctgg ccccggtgca tttttttaaat    3540
acccgcgaga aatagagttg atcgtcaaaa ccaacattgc gaccgacggt ggcgataggc    3600
atccgggtgg tgctcaaaag cagcttcgcc tggctgatac gttggtcctc gcgccagctt    3660
aagacgctaa tccctaactg ctggcggaaa agatgtgaca acgcgacgg cgacaagcaa    3720
acatgctgtg cgacgctggc gatatcaaaa ttgctgtctg ccaggtgatc gctgatgtac    3780
tgacaagcct cgcgtacccg attatccatc ggtggatgga gcgactcgtt aatcgcttcc    3840
```

```
                                                     -continued atgcgccgca gtaacaattg ctcaagcaga tttatcgcca gcagctccga atagcgccct    3900
tccccttgcc cggcgttaat gatttgccca aacaggtcgc tgaaatgcgg ctggtgcgct    3960
tcatccgggc gaaagaaccc cgtattggca aatattgacg gccagttaag ccattcatgc    4020
cagtaggcgc gcggacgaaa gtaaacccac tggtgatacc attcgcgagc ctccggatga    4080
cgaccgtagt gatgaatctc tcctggcggg aacagcaaaa tatcacccgg tcggcaaaca    4140
aattctcgtc cctgattttt caccacccce tgaccgcgaa tggtgagatt gagaatataa    4200
cctttcattc ccagcggtcg gtcgataaaa aaatcgagat aaccgttggc ctcaatcggc    4260
gttaaacccg ccaccagatg ggcattaaac gagtatcccg gcagcagggg atcattttgc    4320
gcttcagcca tacttttcat actcccgcca ttcagag                            4357
```